(12) United States Patent
Busch et al.

(10) Patent No.: US 8,298,782 B2
(45) Date of Patent: *Oct. 30, 2012

(54) REVERSIBLE MHC MULTIMER STAINING FOR FUNCTIONAL PURIFICATION OF ANTIGEN-SPECIFIC T CELLS

(75) Inventors: Dirk H. Busch, Munich (DE); Hermann Wagner, Eching am Ammersee (DE)

(73) Assignee: IBA GmbH, Goettingen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/843,763

(22) Filed: Jul. 26, 2010

(65) Prior Publication Data

US 2011/0070605 A1    Mar. 24, 2011

Related U.S. Application Data

(63) Continuation of application No. 10/451,865, filed as application No. PCT/EP01/15353 on Dec. 28, 2001, now Pat. No. 7,776,562.

(30) Foreign Application Priority Data

Dec. 28, 2000   (EP) ...................................... 00128634

(51) Int. Cl.
  *G01N 33/566*   (2006.01)
  *G01N 33/53*   (2006.01)
  *C12N 11/00*   (2006.01)

(52) U.S. Cl. ........... 435/7.2; 435/7.1; 435/7.5; 435/174; 435/7.21

(58) Field of Classification Search .................... 435/7.2, 435/7.1, 7.5, 174, 7.21
See application file for complete search history.

(56) References Cited

U.S. PATENT DOCUMENTS

| | | | | |
|---|---|---|---|---|
| 4,948,590 A | * | 8/1990 | Hawrot et al. | 424/450 |
| 5,985,658 A | * | 11/1999 | Colinas et al. | 435/325 |
| 6,022,951 A | * | 2/2000 | Sano et al. | 530/350 |
| 7,482,000 B2 | | 1/2009 | Devaux et al. | |

FOREIGN PATENT DOCUMENTS

| | | |
|---|---|---|
| EP | 0835934 A2 | 4/1998 |
| WO | 96/05287 | 2/1996 |
| WO | 97/11183 | 3/1997 |

OTHER PUBLICATIONS

Marelli-Berg, Federica M. et al., Journal of Immunological Methods, 244:205-215 (2000).
Roitt, Ivan et al., Immunolgy, 3rd Edition, Mosby, pp. 6.3-+6.4 (1993).
Voss, Selma and Skerra, Arne, Protein Engineering, 10(8):975-982 (1997).
Werther, K. et al., Journal of Immunological Methods, 238:133-141 (2000).
Yee, Cassian et al., The Journal of Immunology, 162:2227-2234 (1999).

(Continued)

*Primary Examiner* — Rosanne Kosson
(74) *Attorney, Agent, or Firm* — Michael A. Whittaker; Acuity Law Group, P.C.

(57) ABSTRACT

The present invention relates to a new method for reversible staining and functional isolation or characterization of cells, e.g. antigen-specific T cells. With this technique, the original functional status of cells can be substantially maintained after their identification and purification. Thus, this new method is of broad benefit for basic research and clinical applications.

19 Claims, 14 Drawing Sheets

OTHER PUBLICATIONS

Youde, Sarah J., et al., Cancer Research, 60:365-371 (2000).

Davis et al., "Ligand Recognition by alpha beta T Cell Receptors", Annu. Rev. Immunol. 16:523-44 (1998).

Dam et al., "Variable MHC Class I Engagement by LY49 Natural Killer Cell Receptors Demonstrated by the Crystal Structure of Ly49C bound to H-2Kb," Nature Immunology, 4(12):1213-1222 (2003).

DeWildt et al., "Isolation of Receptor-Ligand Pairs by Capture of Long-Lived Multivalent Interaction Complexes," PNAS, 99(13):8530-8535 (2002).

Fritze, Christian E. and Thomas R. Anderson, "Epitope Tagging: General Method for Tracking Recombinant Proteins," Methods in Enzymology, 327:3-16 (2000).

Gloeckner et al., "A Novel Tandem Affinity Purification Strategy for the Efficient Isolation and Characterisation of Native Protein Complexes," Proteomics, 7:1-7 (2007).

Guillaume et al., "Fluorescence-Activated Cell Sorting and Cloning of Bona Fide CD8+ CTL with Reversible MHC-Peptide and Antibody FAB' Conjugates," The Journal of Immunology, 177:3903-3912 (2006).

Harlow, Ed and David Lane, Antibodies: A Laboratory Manual, Cold Spring Harbor Laboratory, pp. 29-35 (1988).

Natarajan et al., "MHC Class I Recognition by Ly49 Natural Killer Cell Receptors," Molecular Immunology, 38:1023-1027 (2001).

Roitt et al., Immunology, Third Edition, Mosby, pp. 6.3-6.4, 1993.

Schlapschy et al., "Functional Humanization of an Anti-CD30 Fab Fragment for the Immunotherapy of Hodgkin's Lymphoma Using and in vitro evolution approach," Protein Engineering, Design & Selection, 17(12):847-860 (2004).

Luxembourg et al., Nature Biotechnology, 16:281-285 (1998).

Communication Pursuant to Article 94(3) EPC dated Nov. 4, 2010, in EPO Application No. 01986941.

* cited by examiner

```
                        SEQUENCE LISTING

<160> NUMBER OF SEQ ID NOS: 6

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Strep-Tag
      peptide
<220> FEATURE:
<223> OTHER INFORMATION: Xaa(2) is any amino acid; Xaa(7) and Xaa(8)
      either both are Gly, or Xaa(7) is Glu and Xaa(8) is Arg
      or Lys

<400> SEQUENCE: 1

Trp Xaa His Pro Gln Phe Xaa Xaa
 1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Strep-Tag
      II peptide

<400> SEQUENCE: 2

Trp Ser His Pro Gln Phe Glu Lys
 1               5

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence:
      streptavidin mutein  (positions 44-47)

<400> SEQUENCE: 3

Ile Gly Ala Arg
 1

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence:
```

```
              Streptavidin mutein (positions 44-47)

<400> SEQUENCE: 4

Val Thr Ala Arg
  1

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence:
      synthetic MHC-binding peptide

<400> SEQUENCE: 5

Gly Tyr Lys Asp Gly Asn Glu Tyr Ile
  1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence:
      synthetic MHC-binding peptide

<400> SEQUENCE: 6

Lys Tyr Gly Val Ser Val Gln Asp Ile
  1               5
```

REVERSIBLE MHC MULTIMER STAINING FOR FUNCTIONAL PURIFICATION OF ANTIGEN-SPECIFIC T CELLS

CROSS REFERENCE TO RELATED APPLICATIONS

This application is a continuation of U.S. patent application Ser. No. 10/451,865, filed Dec. 16, 2003 and issued as U.S. Pat. No. 7,776,562, which is a United States National Stage Entry application based on International Patent Application Serial No. PCT/EP2001/015353, filed Dec. 28, 2001, which claims priority to European Patent Application Serial No. 00128634.3, filed Dec. 28, 2000, each of which is incorporated by reference herein in its entirety.

FIELD OF THE INVENTION

The present invention relates to a new method for reversible staining and functional isolation or characterization of cells, particularly of antigen-specific T cells. With this technique, the original functional status of T cells can be substantially maintained after their identification and purification. Thus, this new method is of broad benefit for basic research and clinical applications.

Identification and purification of antigen-specific T cells without altering their functional status is of great scientific and clinical interest. Methods for direct identification of T cells based on their antigen-specificity (ELISPOT assay (1), intracellular cytokine staining (2), secretion assay [affinity matrix] (3), MHC multimers (2, 4, 5)) have recently been developed. However, most of these identification techniques require in vitro stimulation of T cells, which significantly changes the phenotype and functional status of the cells. To date, only the MHC multimer technology allows the identification and purification of antigen-specific T cells independent of their phenotype, but unfortunately, also conventional MHC multimer staining interferes with functional T cell analysis.

BACKGROUND

Yee et al. (J. Immunol. 162 (1999), 2227-2234) describe the isolation of high avidity melanoma-reactive cytotoxic T lymphocytes (CTL) from heterogeneous populations using peptide-MHC tetramers. The MHC tetramers are biotinylated and irreversibly conjugated to avidin containing a fluorescent labeling group. A removal of the fluorescent marker under physiological conditions is thus not possible. Youde et al. (Cancer Res. 60 (2000), 365-371) describe the use of fluorescence labelled MHC tetramers to isolate human CTLs recognizing endogenous human papilloma virus antigens. Also here biotinylated MHC molecules are used, which are irreversibly bound to streptavidin under physiological conditions so that a removal of the detection reagent from the T cells is not possible.

U.S. Pat. No. 5,985,658 describes a method for separating target cells from a plurality of cells which is based on a reversible high affinity interaction. The method comprises forming a target cell/cell binding reagent/first molecule/second molecule/solid support complex, wherein the cell binding reagent is specific for target cells, e.g. an antibody, wherein the first molecule reversibly binds to the second molecule, wherein one of the first and second molecules is calmodulin, and wherein the other of the first and second molecules is a calmodulin-binding peptide. After removal of non-target cells not attached to the solid support the binding between first and second molecule is reversed, thereby releasing target cells as separate cells from the plurality of starting cells.

The disadvantage of this method is that the target cell binding agent must have a high affinity for the target cell, in order to enable an isolation of the target cell population. Thus, after removal of the binding between first and second molecule the target cell-specific reagent remains bound to the target cell.

Werther et al. (J. Immunol. Meth. 238 (2000), 133-141) describe an antibody-based protocol for the isolation of carcinoma cells from mononuclear cell suspensions. The target cells are stained with an antibody linked to a magnetic bead and thus separated from the starting cell population. The magnetic bead is bound to the target cell via a DNA linker which may be digested with DNase in order to allow a further phenotypical characterization of the target cells. Also this method has the disadvantage that a high affinity target cell binding reagent, i.e. an antibody has to be used, which cannot be easily removed from the target cell.

Marelli-Berg et al. (J. Immunol. 244 (2000), 205-215) describe a protocol for the isolation of endothelial cells from murine tissue. Endothelial cells are labelled by specific antibodies and then purified via binding to microbeads. Also this method includes the above mentioned disadvantages.

BRIEF SUMMARY OF THE INVENTION

We here describe the development of a new method for identification and purification of antigen-specific T cell populations without substantially altering their functional status comprising a reversible staining procedure. More particularly, the reagents used for purifying a target cell population may be completely removed from the target cells. This approach combines the specificity and sensitivity of MHC multimer staining with preserving the functional status of the cells.

T cells recognize processed antigen-fragments (epitopes) in the context of major histocompatibility complexes (MHC) (6). The specificity of T cells is determined by the structure of their T cell receptor (TCR), which is expressed at high levels on the cell surface. Early attempts to use the natural ligand of the TCR—the MHC/epitope complex—for direct identification of epitope-specific T cells were unsuccessful. The failure of this approach can largely be explained by the low affinity of TCR-MHC/peptide interactions, which are especially characterized by a high dissociation rate (FIG. 1A).

Multimerization of MHC/peptide (e.g. to tetrameric molecules) increases the relative avidity of the interaction with TCRs to an extent which allows stable and epitope-specific binding on the T cell surface (FIG. 1B). MHC multimer reagents conjugated with fluorochromes can be used for direct identification of antigen-specific T cells by flow cytometry. This method has revolutionized T cell research over the last few years, allowing to visualize antigen-specific T cell populations for the first time directly ex vivo, in animal models as well as in humans (7, 8).

As long as MHC multimer staining is performed at 4° C., T cells can be identified and purified (FACS, MACS) without altering their original phenotype. However, since MHC multimer reagents represent the natural ligand bound to the TCR, placement of cells into in vitro cell culture or adoptive in vivo transfer into recipients (situations in which the temperature is shifted to 37° C.) results in dramatic alteration of purified T cell populations (FIGS. 3+4), including TCR internalization, activation, overstimulation, and cell death.

Thus, conventional MHC multimer technology allows direct visualization and phenotypic analysis of epitope-specific T cells. However, subsequent functional analysis and in vivo transfer of MHC multimer-stained and purified T cells is complicated by the persistence of TCR-MHC interactions and subsequently induced signaling events. Therefore, the development of methods to remove surface-bound MHC multimers after T cell staining and purification will be of great interest to the field of T cell immunology and is essential for the transfer of MHC multimer technologies to clinical applications and functional diagnostics.

Thus, a subject matter of the present invention is a method for reversible staining of cells comprising the steps:
(a) providing a sample comprising a cell having a receptor molecule,
(b) contacting said cell with
    (i) at least one component specifically binding to said receptor wherein said at least one component is conjugated to at least one first partner of a binding complex, wherein the component and the receptor exhibit a low-affinity interaction,
    (ii) at least one further partner of said binding complex having at least two binding sites for said first partner and
    (iii) a detectable label bound to or capable of binding to (i) and/or (ii), wherein the first partner(s) and the further partner(s) of the binding complex are capable of forming a reversible bond and wherein an aggregate comprising at least two components (i), at least one component (ii) and at least one component (iii) is bound via the receptor molecule to said cell, wherein said cell is stained,
(c) optionally separating said stained cell from other components of said sample and
(d) optionally removing said staining from said cell by disrupting the reversible bond.

A particularly preferred embodiment of the present invention is a method for reversible staining of T cells comprising the steps:
(a) providing a sample comprising a cell having a T cell receptor (TCR) molecule,
(b) contacting said cell with
    (i) at least one TCR binding ligand, e.g. a TCR binding peptide and an MHC molecule conjugated to at least one first partner of a binding complex,
    (ii) at least one further partner of a binding complex having at least two binding sites for the first partner of the binding complex and
    (iii) a detectable label bound to or capable of binding to (i) and/or (ii),
    wherein the first partner(s) and the further partner(s) of the binding complex are capable of forming a reversible bond and wherein an aggregate comprising at least two TCR binding ligands (i), at least one component (ii) and at least one component (iii) is bound via the TCR molecule to said T cell, wherein said T cell is stained,
(c) optionally separating said stained T cell from other components of said sample and
(d) optionally removing said staining from said T cell by disrupting the reversible bond.

The method of the present invention is suitable for reversible staining of cells having a functional receptor molecule, e.g. of T cells, i.e. cells having a functional TCR molecule, wherein said receptor molecule is capable of binding to a receptor ligand, e.g. a peptide/MHC complex. The receptor ligand may be any molecule capable of binding to a receptor molecule present on the cell to be stained, particularly when the receptor ligand and the receptor molecule exhibit a low affinity interaction, e.g. a dissociation constant $K_d$ in the range of $10^{-2}$ to $10^{-7}$ M, particularly of $10^{-3}$ to $10^{-6}$ M. Thus, a single molecule of the receptor ligand is not capable of forming a stable bond with the receptor on the target cell. In order to provide sufficient avidity for the formation of a stable bond between receptor and receptor ligand at least two or more ligand molecules have to bind cooperatively to the receptor molecules on the target cell. This cooperative binding is accomplished by using ligand molecules conjugated to a first partner of a binding pair which is coupled to the further partner of the binding pair which has two or more, e.g. 3, 4, 5 or more, binding sites for first partner-ligand conjugates. If a single ligand molecule has a very low binding affinity, the number of cooperatively bound ligand molecules has to be increased in order to provide sufficient avidity for the formation of a stable bond.

A ligand molecule may be conjugated to one or more first partners of a binding pair. For example, if the ligand molecule is a peptide/MHC complex, a first partner, e.g. a peptide, may be conjugated to an α and/or a β chain of the MHC molecule. More preferably, the ligand molecule comprises at least two first binding partners, for example, a first binding partner may be coupled to the α chain of the MHC molecule and another first binding partner may be coupled to the β chain of the MHC molecule. Alternatively, a sequential arrangement of several first binding partner molecules may be conjugated to a ligand molecule or a subunit of the ligand molecule such as the α and/or β chain of an MHC molecule.

Further examples of suitable receptor molecules having low affinity interactions towards their ligands are cell adhesion receptor molecules such as described in (14) and receptors for costimulatory molecules such as described in (15). Still further examples are low affinity antibodies and fragments thereof and artificially engineered binding molecules such as peptides, lipochalins and other aptamers, e.g. from random libraries which bind molecules located on the cell surface and which exhibit low binding affinity but specific binding characteristics. If the receptor ligand comprises an MHC specific peptide, it is preferred that the peptide is a T cell epitope capable of binding to the TCR receptor of the cell to be analysed and to the MHC molecule. The cell is preferably a mammalian cell, e.g. a mammalian T cell, particularly a human cell, e.g. a human T cell, particularly a subpopulation of mammalian T cells having a predetermined antigen-specifity.

The peptide comprises a T cell epitope capable of binding to a TCR molecule, preferably to a TCR molecule having a predetermined antigen-specifity. The peptide usually has a length of about 8 to about 25 amino acids and preferably comprises so-called anchor amino acid residues capable of allele-specific binding to a predetermined MHC molecule class, e.g. an MHC class I, an MHC class II or a non-classical MHC class. The MHC molecule is preferably a recombinant soluble MHC molecule, which may be prepared in a bacterial expression system (16) or in an insect cell expression system (17).

It is an important feature of the invention that a binding complex, e.g. a binding pair is selected consisting of at least one first partner and at least one further partner wherein the at least further partner has at least two binding sites and more preferably at least four binding sites for the first partner. The bond between the first and the second partner should be reversible, i.e. the bond should be capable of being disrupted under conditions suitable for carrying out the claimed method. Preferably the reversible bond has a $K_d$ between $10^{-2}$ and $10^{-13}$ M, more preferably between $10^{-3}$ and $10^{-10}$ M and most preferably between $10^{-5}$ and $10^{-8}$ M as determined under appropriate conditions, e.g. by fluorescence titration (11). Particularly preferred is a reversible bond having a high $K_{off}$ value, e.g. between $10^{-1}$ sec$^{-1}$ and $10^{-4}$ sec$^{-1}$, especially between $10^{-2}$ sec$^{-1}$ and $10^{-3}$ sec$^{-1}$.

It is a further important feature of the present invention that the staining of the target cell, e.g. the T cell, and the subsequent optional steps, namely the isolation and purification of the stained target cell, e.g. the T cell, and the removal of the staining may be carried out at low temperatures, i.e. at temperatures where substantially no activation and/or signalling events occur, which might result in an alteration of the target cell, e.g. the T cell phenotype. Preferably the staining and the subsequent removal of the staining is carried out at a temperature of $\leq 15°$ C., more preferably $\leq 10°$ C. and most preferably at about 4° C.

The separation of the stained target cell, e.g. the T cell, from other sample components, e.g. unstained T cells may be effected by conventional methods, e.g. cell sorting, preferably by FACS methods using commercially available systems (e.g. FACSVantage by Becton Dickinson or Moflo by Cytomation), or by magnetic cell separation (e.g. MACS by Miltenyi).

The removal of the staining preferably occurs by targeted disruption of the reversible bond between the first and the second partner of the binding complex. This disruption may be achieved by contacting the stained cell with a free first partner of the binding complex or an analog thereof capable of disrupting the bond between the conjugated first partner (i) and the further partner (ii). Preferably, the free first partner is an analog of the conjugated first partner having a higher affinity to the further partner than the conjugated first partner. More preferably, the free first partner has an affinity which is at least 3 orders of magnitude and particularly at least 5 orders of magnitude higher than the affinity of the conjugated first partner. Particularly the free first partner has a dissociation constant $K_d$ which is at least by a factor of $1 \times 10^{-3}$ and especially $1 \times 10^{-5}$ lower.

The label which is used for the detection of stained cells may be any label which is used in diagnostic and analytical methods. Preferably the label does not negatively affect the characteristics of the cells in the method as described. Preferred examples of labels are fluorescent dyes or magnetic labels. The label may be bound to the ligand, e.g. the peptide and/or the MHC molecule, the first partner and/or the further partner of the binding complex. The label may be a direct label, i.e. a label bound to one of the members of the aggregate as specified above. Alternatively, the label may be an indirect label, i.e. a label which is bound to a receptor which in turn is capable of binding to one of the members of the aggregate as specified above.

The removal of the staining from the target cell by disruption of the reversible bond between the first and the second partner results in a loss of the cooperative bond between at least two low-affinity ligands and receptor molecules on the target cell. Thus, the aggregate comprising at least two components (i), at least one component (ii) and at least one component (iii) is completely disrupted. This results in a complete removal of any reagent bound to the target cell, because the bond between the receptor-binding component and the receptor on the target cell is a low-affinity interaction.

The principle of the procedure according to the present invention is explained in the following for a preferred embodiment wherein the binding complex is selected from:
(a) (i) biotin and (ii) a streptavidin or avidin analog capable of reversible binding of biotin,
(b) (i) a biotin analog capable of reversible binding to streptavidin or avidin and (ii) streptavidin or avidin or a streptavidin or avidin analog capable of reversible binding of said biotin analog, and
(c) (i) a streptavidin or avidin binding peptide and (ii) streptavidin or avidin or a streptavidin or avidin analog capable of reversible binding of said streptavidin or avidin binding peptide.

In an especially preferred embodiment oligomers or polymers of streptavidin or of avidin or of analogs of streptavidin or of avidin may be prepared by the introduction of carboxyl residues into a polysaccharide, e.g. dextran essentially as described in "Noguchi, A., Takahashi, T., Yamaguchi, T., Kitamura, K., Takakura, Y., Hashida, M. & Sezaki, H. (1992). Preparation and properties of the immunoconjugate composed of anti-human colon cancer monoclonal antibody and mitomycin C dextran conjugate. Bioconjugate Chemistry 3, 132-137" in a first step. Then streptavidin or avidin or analogs thereof are coupled via primary amino groups of internal lysine residues and/or the free N-terminus to the carboxyl groups in the dextran backbone using conventional carbodiimide chemistry in a second step. For the actually especially preferred 20 embodiment the coupling reaction was performed at a molar ratio of about 60 moles streptavidin or Strep-Tactin® polypeptide (IBA GmbH) per mole of dextran. It should be noted, however, that oligomers or polymers of streptavidin or avidin may also be obtained by crosslinking via bifunctional linkers such as glutardialdehyde or by other methods described in the literature.

The streptavidin binding peptide is preferably selected from the Strep-tag peptides as described in (9), (10) or in U.S. Pat. No. 5,506,121 which are herein incorporated by reference. More preferably, the Strep-tag peptides comprise the amino acid sequence Trp-X-His-Pro-Gln-Phe-Y—Z, wherein X is any desired amino acid and Y and Z either both are Gly, or Y is Glu and Z is Arg or Lys. Especially preferred is the peptide Trp-Ser-His-Pro-Gln-Phe Glu-Lys (Strep-tagII™, IBA GmbH).

In a further preferred embodiment the binding complex may be selected from calmodulin-binding peptides and calmodulin as described in U.S. Pat. No. 5,985,658 or from any other interactions based on the presence of a divalent cation, particularly from peptides binding to a receptor, e.g. the FLAG peptide, which binds to the monoclonal antibody 4E11 as described in U.S. Pat. No. 4,851,341. The disruption of these binding complexes may be accomplished by metal ion chelation, e.g. calcium chelation, e.g. by addition of EDTA.

DETAILED DESCRIPTION OF THE INVENTION

Principle of Procedure

MHC multimers increase the "relative binding avidity" but not the affinity of monovalent TCR-MHC/peptide interactions (FIG. 1A). Since monomeric MHC/peptide complexes do not stably bind to TCRs, a targeted disruption of MHC multimers into MHC monomers results in rapid dissociation of surface bound TCR ligands. After complete dissociation of MHC/peptide complexes (at temperatures where no activation/signaling events occur, preferable at 4° C.), the functional status of the T cell is not changed upon subsequent transfer to cell culture or adoptive in vivo transfer.

The generation of prior art MHC multimer reagents is based on specific biotinylation of soluble MHC complexes. Since streptavidin (SA) has four biotin-binding sites, incubation of biotinylated MHC molecules with (fluorochrome-conjugated) streptavidin at a 4:1 ratio results in the formation of tetrameric MHC reagents (FIG. 1B). The stability of the streptavidin:biotin bond is high ($K_d$<1×10$^{-13}$ M, published to be 4×10$^{-14}$ M in "Weber, P. C., Wendoloski, J. J., Pantoliano, M. W. & Salemme, F. R. (1992). Crystallographic and thermodynamic comparison of natural and synthetic ligands bound to streptavidin. J. Am. Chem. Soc. 114, 3197-3200"), so the reagents are very stable. Addition of biotin (tested up to a concentration of 50 mM) to MHC-streptavidin multimer stained T cells does not significantly affect the stability of the reagents (within a reasonable time window (≦1 day)).

In contrast thereto the method of the present invention is a technique allowing fast and targeted disruption of MHC multimer reagents under physiological conditions for functional isolation of antigen-specific T cells; particularly a substantially complete and fast disruption at low temperatures [preferably at 4° C.]. Further, the procedure is substantially non-toxic to T cells, and the substances used are harmless for (clinical) in vivo applications.

Peptide sequences (Strep-tags) such as disclosed in U.S. Pat. No. 5,506,121 demonstrate binding affinity for the biotin binding site of streptavidin, e.g. with a $K_d$ of approx. between 10$^{-4}$ and 10$^{-5}$ M (9, 10). The binding affinity may be further improved by making a mutations within the streptavidin molecule. Examples of optimized streptavidin muteins (Strep-Tactin® polypeptides, IBA GmbH) are described in U.S. Pat. No. 6,103,493 or (11), which are herein incorporated by reference. Preferably, the streptavidin muteins are characterized in that at position 44 of wild-type streptavidin Glu is replaced by a hydrophobic aliphatic amino acid e.g. Val, Ala, Ile or Leu, at position 45 an arbitrary amino acid is present, at position 46 an aliphatic amino acid and preferably a hydrophobic aliphatic amino acid is present and/or at position 47 Val is replaced by a basic amino acid e.g. Arg or Lys and in particular Arg. More preferably, Ala is at position 46 and/or Arg is at position 47 and/or Val or Ile is at position 44. Most preferably the mutein has a sequence selected from Ile$^{44}$-Gly$^{45}$-Ala$^{46}$Arg$^{47}$ or Val$^{44}$-Thr$^{45}$-Ala$^{46}$-Arg$^{47}$ ("Strep-Tactin®", IBA GmbH as described in (11)). The interaction of the Strep-tag® II peptide (IBA GmbH) with Strep-Tactin® polypeptide (IBA GmbH) is characterized by a binding affinity with a $K_d$ of approx. 10$^{-6}$ M (11) compared to approx. 10$^{-13}$ M for the biotin-streptavidin interaction. Biotin, which still binds with high affinity to Strep-Tactin® polypeptide (IBA GmbH) (with a $K_d$ estimated to be between 10$^{-10}$ M and 10$^{-13}$ M), competes with Strep-tag® II peptide (IBA GmbH) for the binding site.

According to the present invention, stable MHC multimers for antigen specific T cell staining are generated based on the interaction of Strep-tag® II peptide/Strep-Tactin® polypeptide (IBA GmbH). Thus, it is possible to competitively disrupt multimers in the presence of relatively low concentrations of biotin in a rapid manner, preferably less than 2 h, more preferably less than 1 h (FIG. 2).

This system fulfills the required criteria for disruption of MHC multimers (see also above): because of the extreme affinity differences between Strep-tag® II peptide/Strep-Tactin® polypeptide (IBA GmbH) and biotin/Strep-Tactin® polypeptide (IBA GmbH), complete and very fast competitive binding of biotin (even at low temperatures) takes place; biotin (tested up to a concentration of 50 mM) is non-toxic for T cells and does not alter T cell function and small amounts of biotin (vitamin H) are harmless for in vivo applications.

We have tested the Strep-tag® II/Strep-Tactin® polypeptides (IBA GmbH) as a system for both, the generation of MHC multimers and the targeted disruption of multimers bound to the T cell surface by addition of biotin. Alternatively to this approach reversible T cell staining can be achieved by substituting Strep-tags by biotin analogs such as aminobiotin, iminobiotin or desthiobiotin having a lower affinity for streptavidin or avidin compared to biotin. A still further preferred embodiment relates to the competition of free biotin for the binding of biotinylated MHC molecules to Strep-Tactin® polypeptide (IBA GmbH) or other streptavidin analogs having lower affinity for biotin.

Alternatively, other streptavidin-binding peptides known in the art may be used, e.g. as described by Wilson et al. (Proc. Natl. Acad. Sci. USA 98 (2001), 3750-3755).

As one key element of the present invention is the fact that the reversible bond can be disrupted in a targeted manner with the addition of small amounts of the physiological compound biotin (vitamin H) which seems neither to be detrimental to living cells nor to alter their functional state, we claim every binding complex which can be selectively disrupted with that compound or analogs thereof. Thus, apart from the binding complexes between streptavidin or avidin or analogs thereof and biotin or biotin analogs or streptavidin- or avidin-binding peptides also other binding complexes are suitable for the purpose of the invention, provided they allow reversible staining of a cell which can be disrupted by the addition of compounds such as biotin or biotin analogs which do not show any detrimental effect to the cell to be stained. For example, an antigen/antibody-binding pair can be applied, particularly if a polymerized or oligomerized antibody is used. Further examples of such binding complexes besides streptavidin/avidin and their analogs and/or antibodies may be so called engineered protein scaffolds for molecular recognition as published in "Skerra A. (2000). Engineered protein scaffolds for molecular recognition. J. Mol. Recognit. 13, 167-187" after being engineered to recognize compounds which may be disrupted in a targeted manner by disruption using biotin or biotin analogs.

Further, the present invention relates to a substantially pure target cell population which is defined by the presence of a specific common receptor and which has been purified from a heterogeneous cell population (i.e. heterogeneous relating to the presence or absence of the specific common receptor) using an affinity reagent binding to said common receptor. The target cell population is characterized in that the affinity reagent has been substantially completely removed (preferably below the detection limit) from said receptor. The complete removal of the affinity reagent is accomplished by using the reversibly multimerized low affinity ligand as described above. Thus, a target cell population is provided having a functional status (defined by the common specific receptor) which has not been altered by the purification method. The common specific receptor which defines the target cell population may be any receptor against which a low affinity ligand as described above may be directed. For example, the receptor may be an antigen defining a cell population or subpopulation, e.g. a population or subpopulation of blood cells, e.g. lymphocytes, monocytes or natural killer cells, bone marrow cells or stem cells, e.g. CD34-positive peripheral stem cells. On the other hand, the receptor may also be a marker for tumor cells.

Particularly, the present invention relates to a substantially pure antigen-specific T cell population having a functional status which is substantially unaltered by a purification procedure comprising staining the desired T cell population, isolating the stained T cell population from a sample comprising non-stained T cell population and removing said stain, i.e. the functional status of the T cell population before purification is substantially the same as after the purification. This T cell population may be obtained by the method as described above. More particularly, a T cell population is provided which is substantially free from any binding reagents used for the isolation of the population, e.g. antibodies or TCR binding ligands such as multimeric TCR binding ligands.

Finally, the present invention relates to a fusion polypeptide comprising (a) at least one peptide domain which is a first partner of a binding complex which is capable of forming a reversible bond with at least one further partner of the binding complex and (b) a ligand domain which binds specifically but with low affinity to a receptor on a cell surface. The fusion polypeptide is preferably a genetic fusion, wherein one or several sequentially clustered peptide domains are located on the N- and/or C-terminus of the ligand domain. The fusion polypeptide may also consist of several subunits, wherein each subunit forms a ligand subdomain which bind together to the receptor. In this case each subunit preferably contains at least one peptide domain. In a preferred embodiment the fusion polypeptide comprises (a) a streptavidin-binding peptide and (b) an MHC molecule, preferably a soluble MHC molecule. For example, the streptavin-binding peptide may be fused to the N-terminus and/or the C-terminus of the α-chain and/or the β-microglobulin chain of an MHC molecule. For example, fusion polypeptides comprising at least two streptavidin-binding peptides, e.g. fusion polypeptides having a streptavidin-binding peptide bound both to the C-terminus of the α-chain and the β-chain have been shown to be suitable for the purpose of the present invention. Preferred streptavidin-binding peptides are Strep-tag peptides as described above, particularly Strep-tag® II peptide (IBA GmbH). Further, the invention relates to nucleic acids encoding a fusion polypeptide as described above, wherein the nucleic acids are preferably located on a recombinant vector, particularly an expression vector allowing expression of the claimed fusion polypeptide in a suitable host cell, e.g. a eukaryotic or prokaryotic host cell.

The method of the present invention allows a functional isolation of target cell populations, e.g. of antigen specific T cell populations based on a reversible staining procedure. The original functional status of target cells, e.g. T cells, can be substantially maintained after the identification and purification. Thus, the method of the invention is of broad benefit for basic research and clinical applications. Examples of preferred applications are as follows:

Basic Research:
  Direct ex vivo investigation of the functional status of antigen-specific T cell populations. The functional status of T cell populations in vivo is suggested to be highly diverse and dependent on specific in vivo conditions, but because of the lack of appropriate investigative tools, these aspects are only marginally understood. With MHC multimer techniques, epitope-specific T cell populations can be identified and purified independent of their functional status. However, the binding of multimer reagents interferes with subsequent functional assays. Reversible T cell staining e.g. using MHC-Strep-tag® II peptide/Strep-Tactin® polypeptide (IBA GmbH) reagents is the first technology allowing the direct functional ex vivo investigation of unaltered diverse T cell populations.
  Purification of antigen-specific T cell populations for highly efficient in vitro expansion. The characterization of T cell populations obtained ex vivo often requires further in vitro expansion to T cell lines or T cell clones. With MHC multimer techniques, single cells or distinct phenotypic subpopulations within a diverse T cell population can be isolated, but the binding of the reagents to the TCR interferes with the efficiency of in vitro expansion. This experimental problem is solved by reversible T cell staining using the reagents of the invention, e.g. MHC-Strep-tag® II peptide/Strep-Tactin® polypeptide (IBA GmbH) reagents.
  Purification of antigen-specific T cell populations for adoptive transfer experiments. Many in vivo experiments in immunological research require the adoptive transfer of purified T cells into recipient animals. Both, the purity of the transferred T cell populations and possible changes in the cells that occur during the isolation procedure are concerns in these experimental systems. The highest purity of cell populations is achieved by positive selection methods, but the markers (usually antibodies) used for identification are difficult to remove from the surface of isolated cells and can interfere with the outcome of subsequent in vivo experiments. Reversible T cell staining using the reagents of the invention, e.g. MHC-Strep-tag® II peptide/Strep-Tactin® polypeptide (IBA GmbH) reagents allows the combination of positive selection methods with later removal of the selection marker and might greatly improve adoptive transfer experiments.
  TCR-MHC affinity measurements. Diversity of epitope-specific T cell populations is reflected on the level of TCR-MHC/peptide binding affinities. While the measurement of TCR-MHC/peptide binding affinities of T cells is still very difficult, several recent studies indicate that MHC/peptide dissociation rates correlate with relative binding affinities (12, 13). With the reagents of the invention, e.g. MHC-Strep-tag® II peptide/Strep-Tactin® polypeptide (IBA GmbH) reagents, MHC/peptide complexes can be accumulated on the cell surface of epitope specific T cells and MHC dissociation rates can be determined after fast monomerization by addition of biotin. This is possible because removal of the Strep-Tactin® polypeptide (IBA GmbH) backbone is significantly faster than MHC dissociation rates.

Clinical Applications:
  Purification of antigen-specific T cell populations for highly efficient in vitro expansion. Generation of human T cell lines or clones (e.g. pathogen/tumor-specific or autoreactive T cells) is necessary in many areas lo of clinical research, diagnostics, and immunotherapy. In vitro culture is often limited by difficulties in standardizing conditions for antigen-specific stimulation. Improved strategies for the purification of antigen-specific T cell populations could greatly enhance the efficiency of in vitro expansion, allowing the use of antigen-independent stimulation such as mitogens and anti-CD3. With the invention, e.g. with MHC-Strep-tag® II peptide/Strep-Tactin® polypeptide (GmbH) reagents, antigen-specific T cell populations can be isolated directly ex vivo and expanded in vitro after dissociation of the reagents. This approach is expected to be much more efficient than purification using conventional MHC multimer reagents, as the binding of the reagents negatively interferes with the efficiency of in vitro T cell expansion.
  Purification of antigen-specific T cell populations from in vitro expanded cell lines or clones for further functional analyses or therapy. In vitro expansion of T cells requires the addition of antigen-presenting cells or feeder cells to the culture. For further functional analysis, and especially for therapeutic applications (e.g. adoptive transfer), it would be helpful to remove these contaminating cells. For positive selection procedures (which usually result in the highest degrees of purity), the selection marker should be removable from the T cell surface, as it might interfere with functional assays or adoptive transfer. If T cells are used for in vivo applications the selection marker must be further removed if it contains substances that could cause clinical complications such as allergic reactions. Reversible T-cell staining e.g. using MHC-Strep-tag® II peptide/Strep-Tactin® polypeptide (IBA GmbH) reagents fulfills all these criteria.

Ex vivo purification of antigen-specific T cell populations for "direct adoptive immunotherapy". The isolation of antigen-specific T cell populations directly ex vivo followed by immediate transfer of the cells into recipients (without any further in vitro propagation) is of special clinical interest. It is expected that directly isolated cell populations are much more efficient than cultured cells for in vivo applications. Extremely high numbers of in vitro expanded T cells are required for effective adoptive transfers, a phenomenon most likely due to the adaptation of T cells to in vitro culture conditions. An example for an important clinical application for this procedure is the parallel purification and adoptive transfer of EBV- and/or CMV-specific T cell populations during [otherwise] T cell-depleted stem cell transplantations, a protocol which is likely to dramatically reduce the incidence of EBV and CMV-related malignancies in transplant patients. Reversible T cell staining and isolation e.g. using MHC-Strep-tag® II peptide/Strep-Tactin® polypeptide (IBA GmbH) reagents could be an ideal method for these clinical applications.

Functional T cell diagnostics. MHC multimer techniques allow quantification and phenotypic characterization of antigen-specific T cells directly ex vivo. However, binding of multimer reagents to the TCR complicates the use of purified cells in functional assays (e.g. chronic virus infections [HIV, CMV, EBV, HBV, HCV], tumor-specific T cell populations). Reversible T cell staining and isolation e.g. using MHC-Strep-tag® II peptide/Strep-Tactin® polypeptide (IBA GmbH) reagents opens the door for powerful evaluation of antigen-specific T cell status in many clinical situations.

Further, the present invention is explained in more detail by the following figures and examples.

Figure 1:
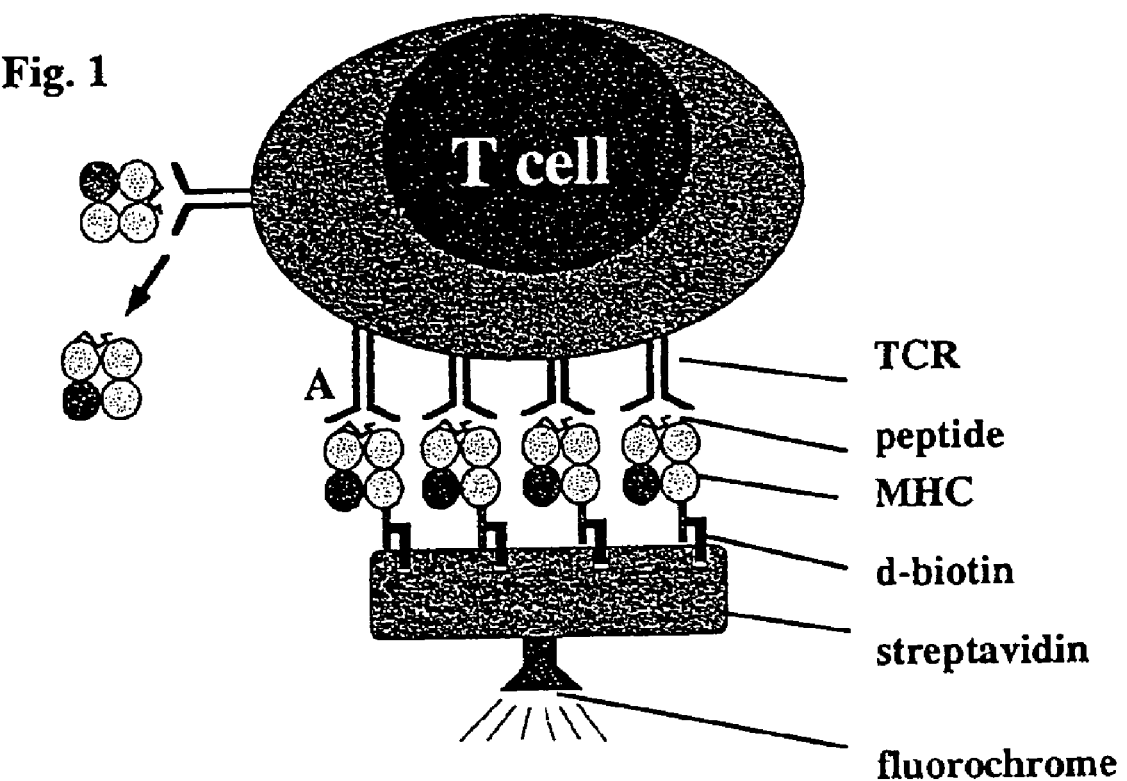
FIG. 1: The binding of monomeric and multimeric peptide/MHC conjugates to the TCR of T cells. Due to the binding of the peptide/MHC complex to the TCR, the functional status of the T cells is dramatically altered under physiological conditions (prior art).

of differently treated T cells in response to $LLO_{91-99}$ peptide-coated target cells (peptide titration, x-axis) with an effector to target cell ratio of approx. 5:1, compare with FIG. 1c. (c) Proliferation (y-axis) of differently treated T cells stimulated with epitope or various mitogens (indicated on the x-axis) in the presence of syngeneic irradiated splenocytes. Compare with FIG. 1d. (d) Protection against *Lysteria monocytogenes* infection following adoptive transfer of $4.1 \times 10^6$ $LLO_{91-99}$-specific T cells treated with binding ($LLO_{91-99}$) or non-binding ($p60_{217-225}$) MHC multimer reagents (indicated to the left). Two groups of mice were injected with cells previously incubated with binding MHCstreptagII reagents (striped bars) and either washed (upper bar, large stripes) or not washed (lower bar, small stripes) in the presence of d-biotin. Control mice received cells treated with binding (open bar) or non-binding (filled bar) conventional MHC tetramer reagents (plus d-biotin wash) or were injected with NaCl only (grey bar). Numbers of viable bacteria (y-axis) were determined 48 h following Lysteria infection. Data are representative of three independent experiments, each with 2 mice per group.

Figure 8:
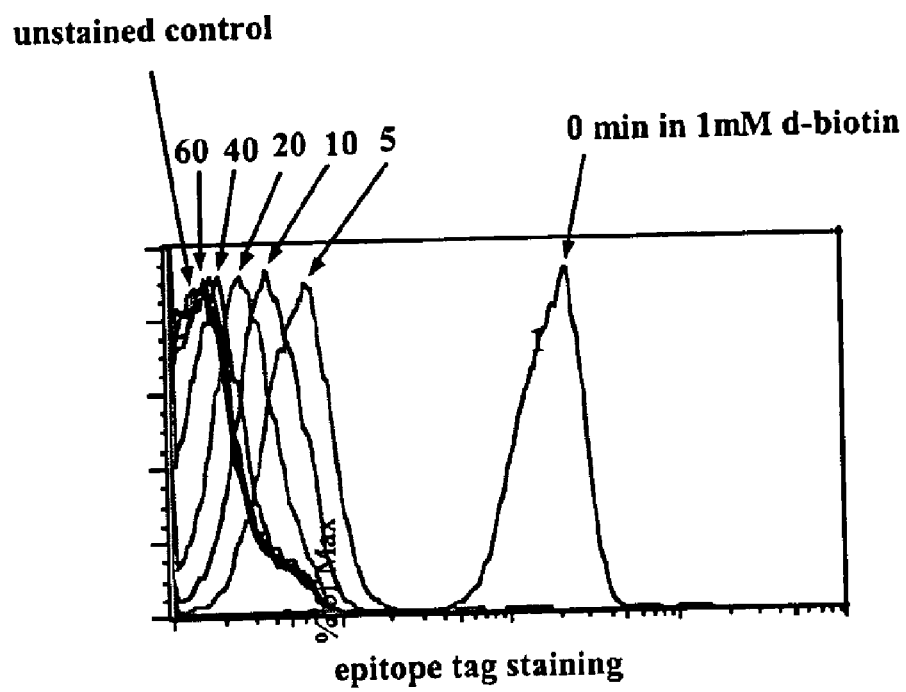

FIG. 8: Reversible MHC multimer staining can be transferred to human T cells. HLA*A0201streptagII fusion proteins were generated and folded in the presence of recombinant human $\beta_2$ microglobulin-HSVtag-streptagII and the epitope $MART1_{27-35}$ to obtain soluble MHC molecules. These were subsequently multimerized with streptactin-polymers and used for staining of a $MART_{27-35}$-specific T cell clone (kindly provided by Burkhard Schmidt, Institute of Hematology, Klinikum rechts der Isar, Munich). $MART1_{27-35}$-specific T cells were stained for 30 min at 4° C. with HLA*A0201 streptagII-Streptactin multimer reagents; after washing, aliquots of the stained cells were incubated for different periods of time in the presence of 1 mM d-biotin, all done at 4° C. Secondary staining for HSV-epitope was performed as described before (see also legend to FIG. 3); then cells were fixed in 1% paraformaldehyde and analyzed by flow cytometry. Histograms show fluorescence intensity for HSV epitope tag staining.

EXAMPLES

1. Materials and Methods

Generation of H2-$K^d$ Strep-Tag® II Peptide (IBA GmbH) Fusion Proteins

The pET3a/H2-$K^d$ expression vector (5) was mutated by standard PCR techniques to exchange the C-terminal biotinylation site to the Strep-tag® peptide (IBA GmbH) sequence. Protein expression was induced in the expression host 25 BL21(DE3) by addition of IPTG and subsequently, inclusion bodies were purified as described before (5).

In Vitro Refolding and Generation of Multimeric MHC Strep-Tag® II Peptide (IBA GmbH) Reagents H2-$K^d$ Strep-tag® peptide (IBA GmbH) and mouse f$\beta_2$-microglobulin (containing a HSV epitope tag at the C-terminus) inclusion bodies were dissolved in 8 M urea and thereafter refolded by rapid dilution into arginine-rich buffer in the presence of high amounts of synthetic MHC binding peptide (here: 0.5 mg/ml $LLO_{91-99}$, GYKDGNEYI or $p60_{217-225}$, KYGVSVQDI, respectively) as described previously (5). Soluble MHC complexes were further purified by gel filtration (Superdex® 200HR resin, Pharmacia) and aliquots were stored in liquid nitrogen. For multimerization StrepTactin® polypeptide (IBA GmbH) polymers were incubated overnight with soluble H2-$K^d$ Strep-tag® II peptide/$LLO_{91-99}$ complexes (IBA GmbH) at a molar ratio of 2:1 or 1:1 (2 MHC molecules or 1 MHC molecule per 1 Strep-tag® binding site).

Generation of Conventional Multimeric MHC Reagents

Conventional tetramers were generated using PE- or $Alexa_{546}$-conjugated streptavidin (MolecularProbes). MHC multimer reagents were stored at 2 mg/ml in PBS pH 8.0 containing 0.02% NaAzide, 0.1 mM EDTA, 1 μg/ml pepstatin, and 1 μg/ml leupeptin (5).

Generation and Staining of T Cell Lines, Functional Assays $LLO_{91-99}$ specific T cell lines were expanded in vitro as described before (18). MHC-multimer staining was performed by incubation of approximately 2 μg H2-$K^d$ Strep-tag® II peptide multimer reagent (IBA GmbH) per $1 \times 10^6$ cells at 4° C. for 30 min. For epitope-tag staining cells were washed, fixed briefly in 1% paraformaldehyde, and subsequently stained for anti-HSV tag using an unconjugated primary mouse or rat mAb (e.g. TB067, Novagen) and a secondary anti-mouse or anti-rat-PE antibody (e.g. A85-1, PharMingen). Flow cytometry was performed using a FACSCalibur (Becton Dickinson) and FlowJo software. For dissociation experiments stained cells were washed several times (usually 10 times) in 1 mM biotin buffer (PBS, 5% FCS) usually at 4° C. Conventional $^{51}$Cr-release and $^3$H-thymidine incorporation assays were performed as described before (18).

Adoptive Transfer Experiments $LLO_{91-99}$ specific T cells were stained with H2-$K^d$ Strep-tag® II peptide multimer reagents (IBA GmbH) at 4° C. (30 min) and subsequently washed extensively in biotin-free medium. Dissociation by addition of biotin was done as described above (control cells were treated equally in the absence of biotin). Adoptive cell transfer was performed by injection of $1 \times 10^7$ cells—per mouse per group—into the tail vein of naive BALB/c mice. 48 h after i.v. injection with $5 \times LD_{50}$ *Listeria monocytogenes* strain 43251 ($2 \times 10^4$ cells) the number of bacteria per organ (spleen and liver) was measured by plating out serial dilutions of tissue homogenate.

2. Results

Interference of MHC Multimer Staining with T Cell Function In Vitro

Phenotypic changes of cell populations have not been reported so far following epitope-specific T cell staining at low temperatures (4° C.). Under these conditions, TCR-MHC mediated signalling events become not activated. MHC multimer staining at higher temperatures (e.g. at room temperature (RT), or at 37° C.) has been performed to improve the intensity and/or stabilty of the fluorescent signal through epitope-specific internalization of the multimer. In order to analyze the impact of differential treatment of T cells on their phenotype, we compared $LLO_{91-99}$-specific T cell lines following staining with $LLO_{91-99}$/H2-$K^d$ tetramers at 4° C. or 37° C. As a negative control, MHC tetramers containing different *Listeria* epitope ($p60_{217-227}$) were used; these reagents cannot bind to TCRs of $LLO_{91-99}$-specific T cells, thus controlling for potential peptide-independent effects. After 2 h of incubation at 4° C., all $LLO_{91-99}$-specific T cells exhibited high intensity staining (FIG. 3a, upper histogram), whereas incubation at 37° C. resulted in a reduced and more diffuse staining pattern. These changes correlated with substantial downregulation of surface TCR (FIG. 3a, middle histogram) and increased binding of annexin V, an early marker of apoptosis (FIG. 3a, lower histogram), after staining at 37° C. Immunofluorescence microscopy (FIG. 3) reveals a typical surface-staining pattern of $LLO_{91-99}$/H2-$K^d$ tetramers after incubation at 4° C., whereas most multimers are internalized at 37° C. No phenotypical changes were detectable using non-binding MHC multimer reagents.

Figure 3A:
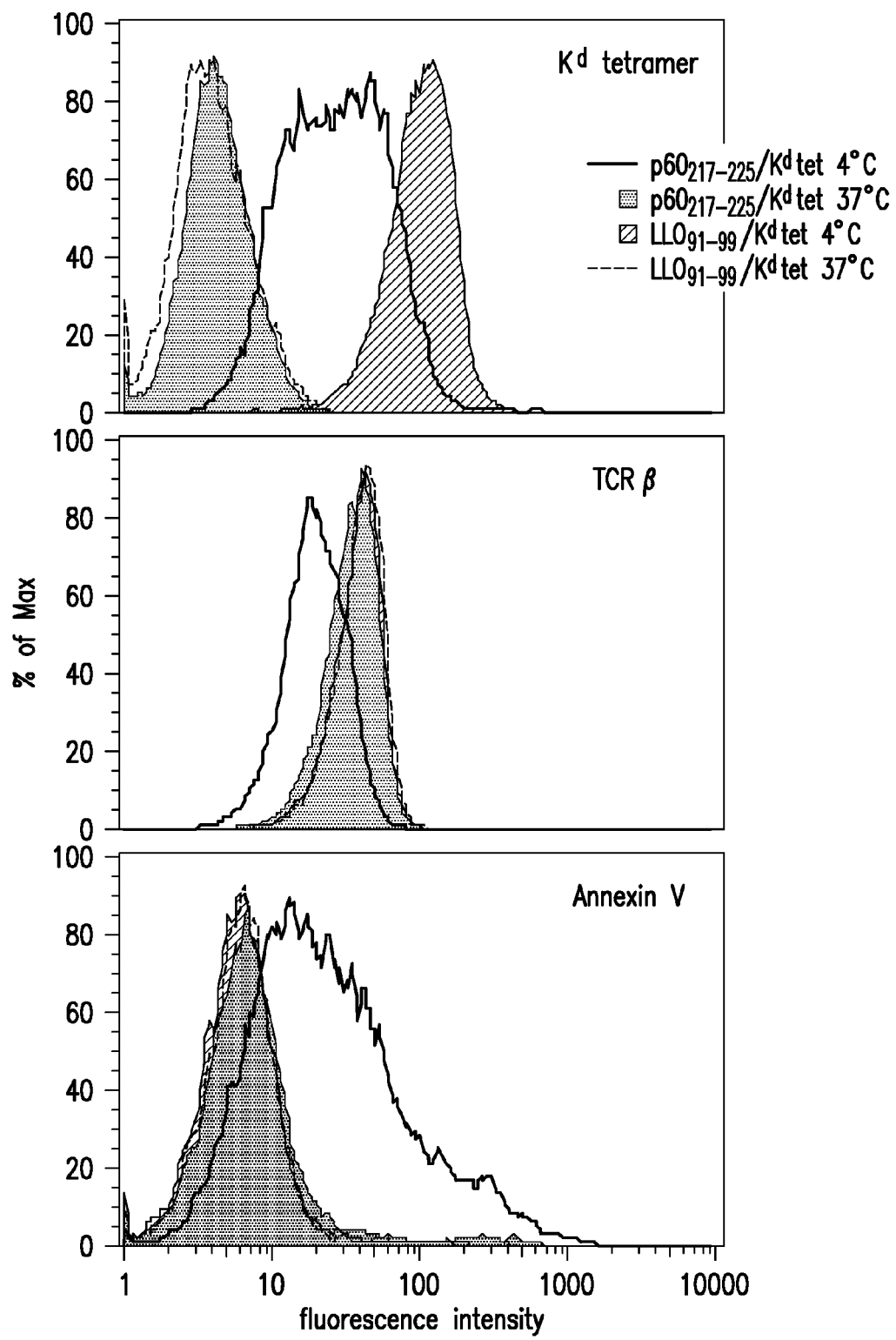
FIG. 3: Interference of MHC multimer staining with T cell function in vitro. (a) $LLO_{91-99}$-specific T cells were stained for 2 hours with binding ($LLO_{91-99}$/H2-$K^d$) or non-binding ($p60_{217-225}$/H2-$K^d$) streptavidin-PE tetramer ("tet") reagents at 4° C. or 37° C. MHC tetramer staining (upper), TCR expression (middle, filled black graph hidden behind $TCR^{high}$ populations), and annexin V binding (lower) are shown in histogram format. (b) Immunofluorescence staining of $LLO_{91-99}$-specific T cells one hour after incubation with $LLO_{91-99}$/H2-$K^d$ streptavidin-Alexa$_{546}$ tetramers (red) at 4° C. or 37° C. (c) $LLO_{91-99}$-specific T cells stained for 30 min with binding or non-binding tetramer reagents at 4° C., were then washed to remove unbound reagent and transferred to a chromium release assay (effector to target ratio approx. 5:1). $LLO_{91-99}$ peptide concentration and percent specific lysis are shown on the x- and y-axes, respectively. The bars indicate lysis of MHC mismatched target cells ($10^{-8}$ M $LLO_{91-99}$ peptide and no peptide conditions only) by effector cells treated with non-binding MHC tetramer reagents (filled bars) or binding reagents (open bars). (d) $LLO_{91-99}$-specific T cells were treated as in (c), transferred into a proliferation assay in the presence of syngeneic irradiated splenocytes, and stimulated in the presence of peptide or various mitogens (x-axis).
Figure 3B:
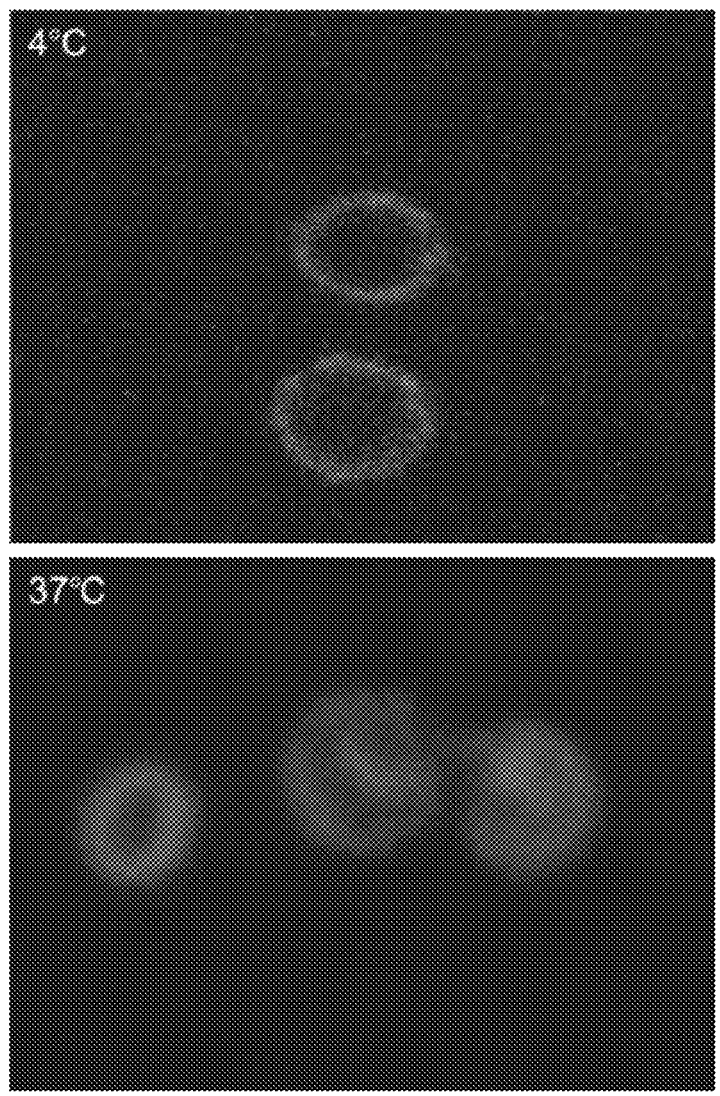
Figure 3C:
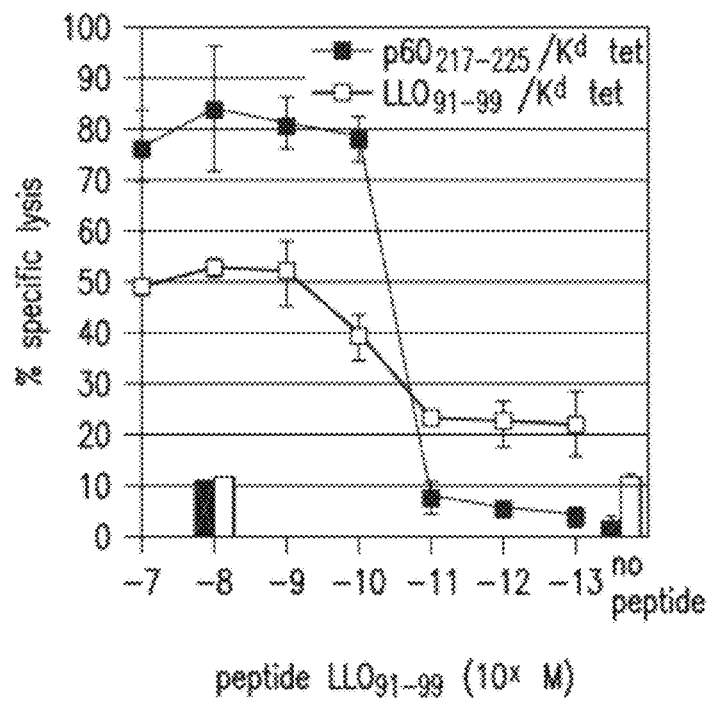
Figure 3D:
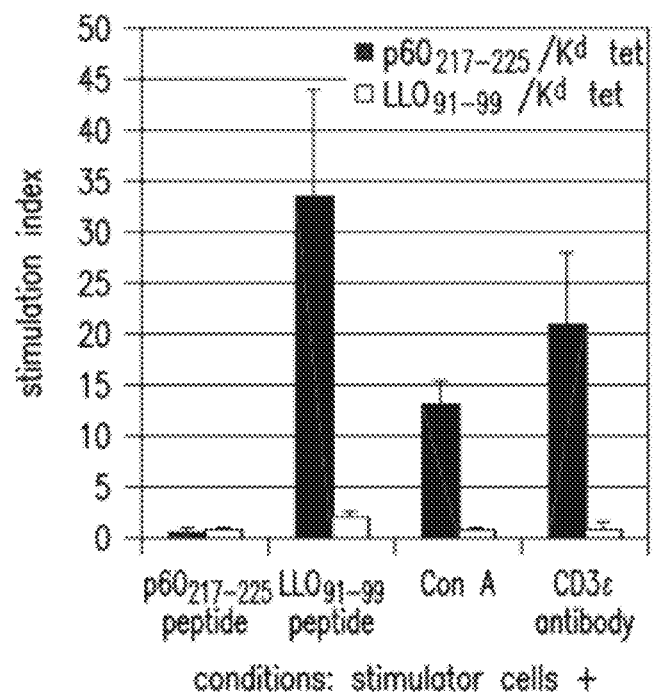
Figure 7A:
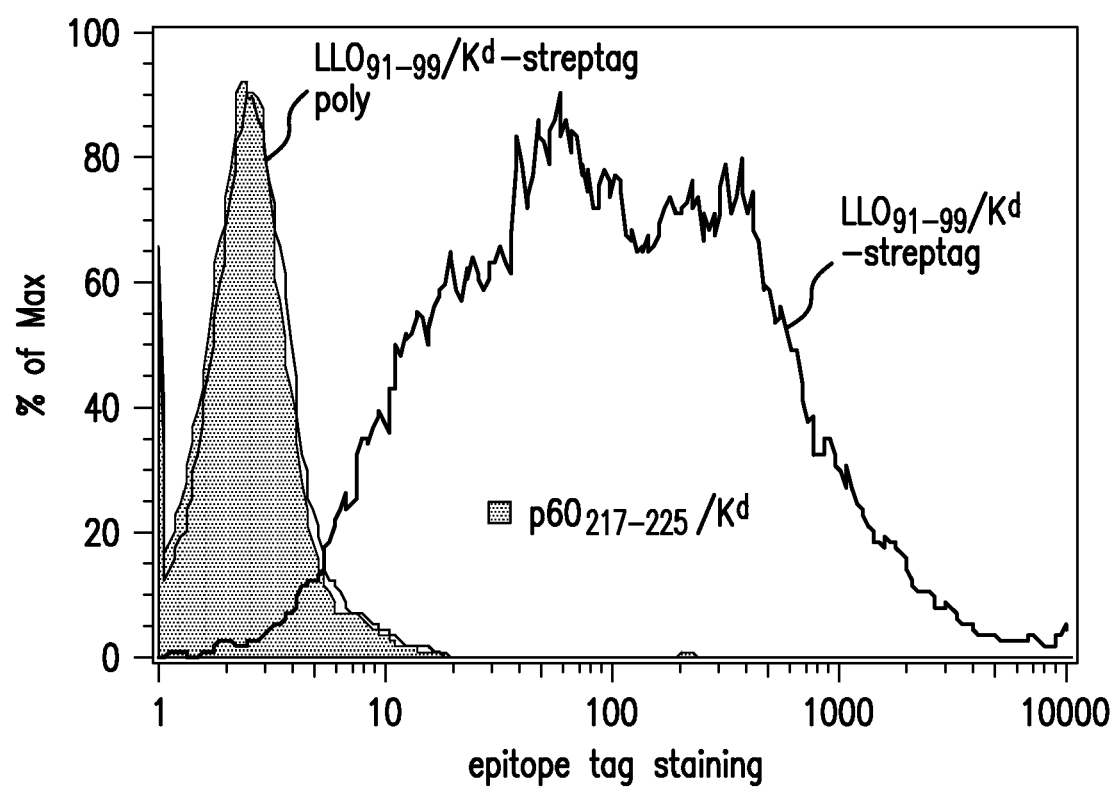
FIG. 7: Reversible MHC multimer staining and T cell function. $LLO_{91-99}$-specific T cells were stained for 30 min with binding $LLO_{91-99}$/H2-$K^d$ Strep-tag® II peptide/β$_2$m-Strep-tag® II peptide-HSV-tag:Strep-Tactin® polypeptide (IBA GmbH) or non-binding ($p60_{217-225}$/H2-$K^d$) multimer reagents and then extensively washed over 4 h in the presence or absence or d-biotin (1 mM, all done at 4° C.) prior to assays or adoptive transfer. (a) Staining for recombinant MHC-molecules (detected by epitope-tag staining, x-axis) on differently treated T cells. (b) Cytotoxicity (% specific lysis, y-axis)

To investigate if MHC multimer staining also interferes with T cell function, we compared the cytolytic capacity of differently treated cytotoxic T cells (CTLs). CTLs were stained with specific MHC tetramers or control reagents, then they were extensively washed to remove unbound MHC molecules, and subsequently incubated at 37° C. at a constant effector to target cell ratio in the presence of various concentrations of $LLO_{91-99}$ peptide. Labelling with CTLs with MHC tetramers dramatically affects their cytotoxicity profile (FIG. 3c): (1) reduction in maximum % specific lysis (the extent of reduction varied between experiments, see also FIG. 7b), (2) decreased peptide sensitivity, and (3) increased lysis in the absence of $LLO_{91-99}$ peptide addition. The reduction in maximum lysis and decreased peptide sensitivity seems mostly due to TCR internalization and early apoptotic events (see also FIG. 3a). The increase in spontaneous lysis is—at least in part—mediated by 'bystander effects', since also MHC mismatched cell lines are affected (FIG. 3c, bars); MHC tetramer-induced release of cytolytic substances might affect the viability of neighboring target cells. Even more dramatic is the negative impact of MHC multimer staining on further in vitro expansion of epitope-specific T cells. $LLO_{91-99}$/H2-10 tetramer treated cells (FIG. 3d) poorly proliferate in response to antigen or mitogenic stimulation, likely due to loss of T cells through MHC multimer-induced overstimulation causing apoptosis (FIG. 3a). Taken together, these findings demonstrate that MHC multimer staining induces substantial phenotypical and functional changes of epitope-specific T cells at physiological temperatures (37° C.).

Interference of MHC Multimer Staining with T Cell Function In Vivo

Figure 4:
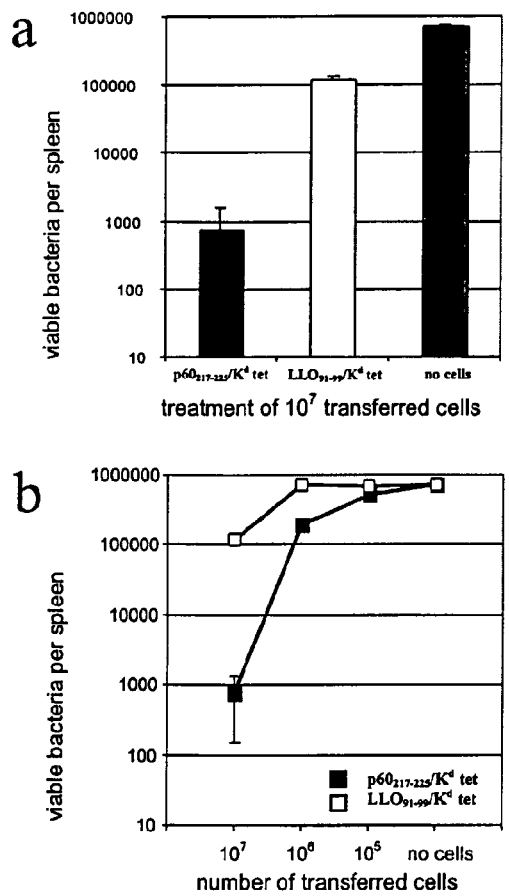
FIG. 4: Interference of MHC multimer staining with T cell function in vivo. $LLO_{91-99}$-specific T cells were stained for 30 min with binding ($LLO_{91-99}$/H2-$K^d$) or non binding ($p60_{217-225}$/H2-$K^d$) tetramer ("tet") reagents, extensively washed to remove unbound reagent, and transferred into naïve recipient mice. Six hours later, mice were infected with $2 \times 10^4$ Listeria monocytogenes. Numbered viable bacteria (y-axis) determined in the spleen 48 h post-infection are shown following adoptive transfer of $1 \times 10^7$ $LLO_{91-99}$-specific T cells (a) or various numbers of $LLO_{91-99}$-specific T cells (b) treated with binding ($LLO_{91-99}$/H2-$K^d$, open bar) or non-binding ($p60_{217-225}$/H2-$K^d$, filled bar) tetramer reagents (2 mice per group, standard deviations indicated). Control mice received NaCl only. (c) $LLO_{91-99}$/H2-$K^d$ tetramer staining (y-axis) after transfer of $1 \times 10^7$ differently treated T cells (same as in (a)); dot plots are gated on CD8+ T cells, with staining for CD62L, an activation marker downregulated on activated T cells, shown on the x-axis.
Figure 4:
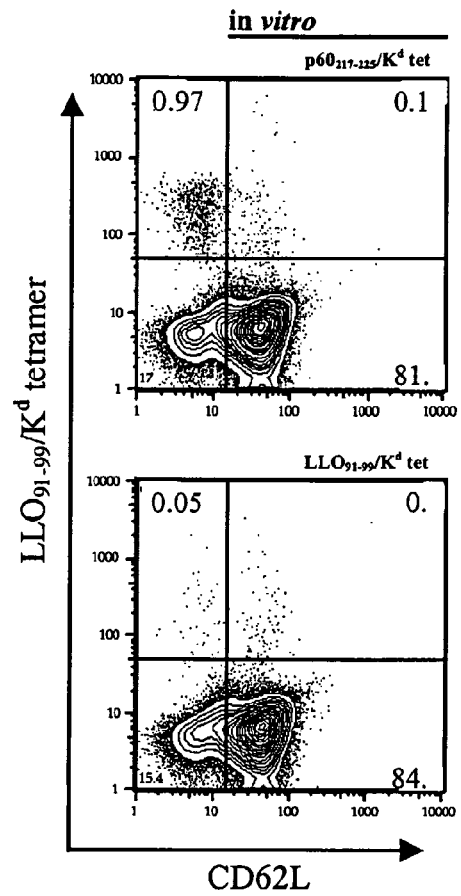

In order to investigate whether MHC multimer staining also affects in vivo function, we adoptively transferred differently treated T cells into naïve recipient mice and subsequently monitored protection against primary infection with *Listeria monocytogenes*. In negative control BALB/c mice, high numbers of viable bacteria are detectable in the spleen 48 hours after infection (FIG. 4a, grey bar). Adoptive transfer of $1×10^7$ $LLO_{91-99}$-specific CTLs treated with non-binding control MHC tetramers confers *Listeria*-specific protection (black bar). However, pretreatment of transferred cells with binding $LLO_{91-99}$/H2-$K^d$ tetramer reagents results in a dramatic loss of protective capacity. The degree of protection correlates with the number of transferred cells (FIG. 4b); while $1×10^7$ CTLs pretreated with binding MHC tetramers still confer some significant *Listeria*-specific protection *Listeria* infection in mice who received $1×10^6$ cells is indistinguishable from untreated mice. Adoptive transfer of $1×10^6$ control CTLs still mediates significant protection. After cell transfer, much lower numbers of $LLO_{91-99}$-specific T cells could be recovered from recipient mice who received MHC multimer-stained cells as compared to control cells (FIG. 4c); the same results were obtained tracking the transferred T cells with the allotypic surface marker thy1.1 (data not shown). These data reveal a strong negative impact of MHC multimer staining on in vivo cell transfer, both in terms of survival and function.

Development of a Reversible MHC Multimer Staining Technology

Figure 2:
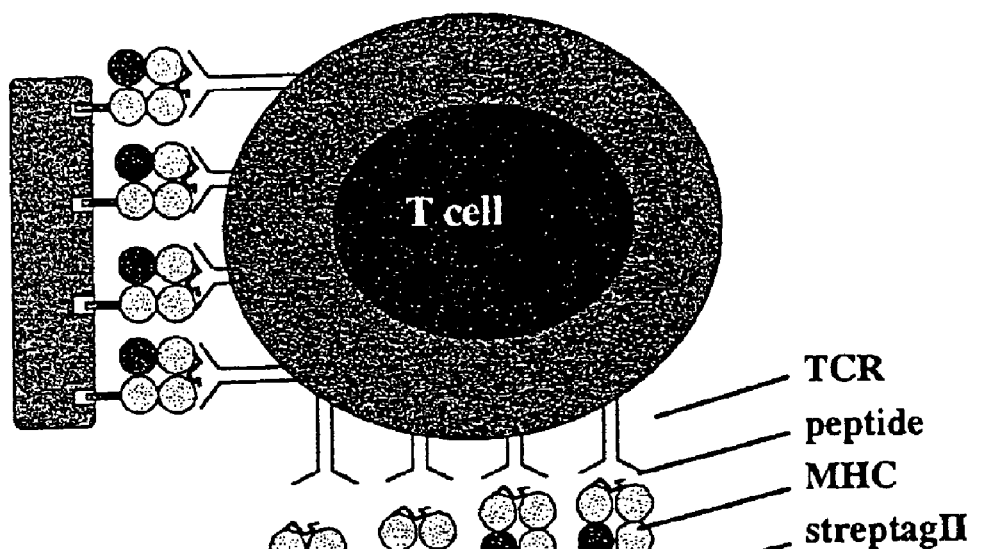
FIG. 2: By targeted disruption of peptide/MHC multimer binding to the TCR molecules the staining is removed resulting in a purified T cell population having substantially unaltered characteristics (invention).
Figure 2:
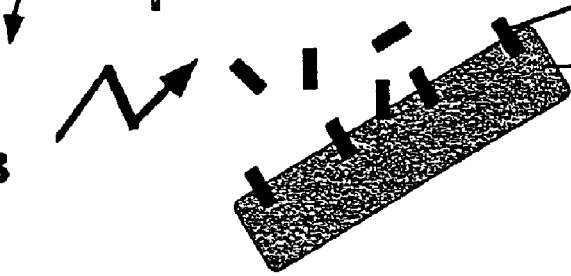
Figure 5A:
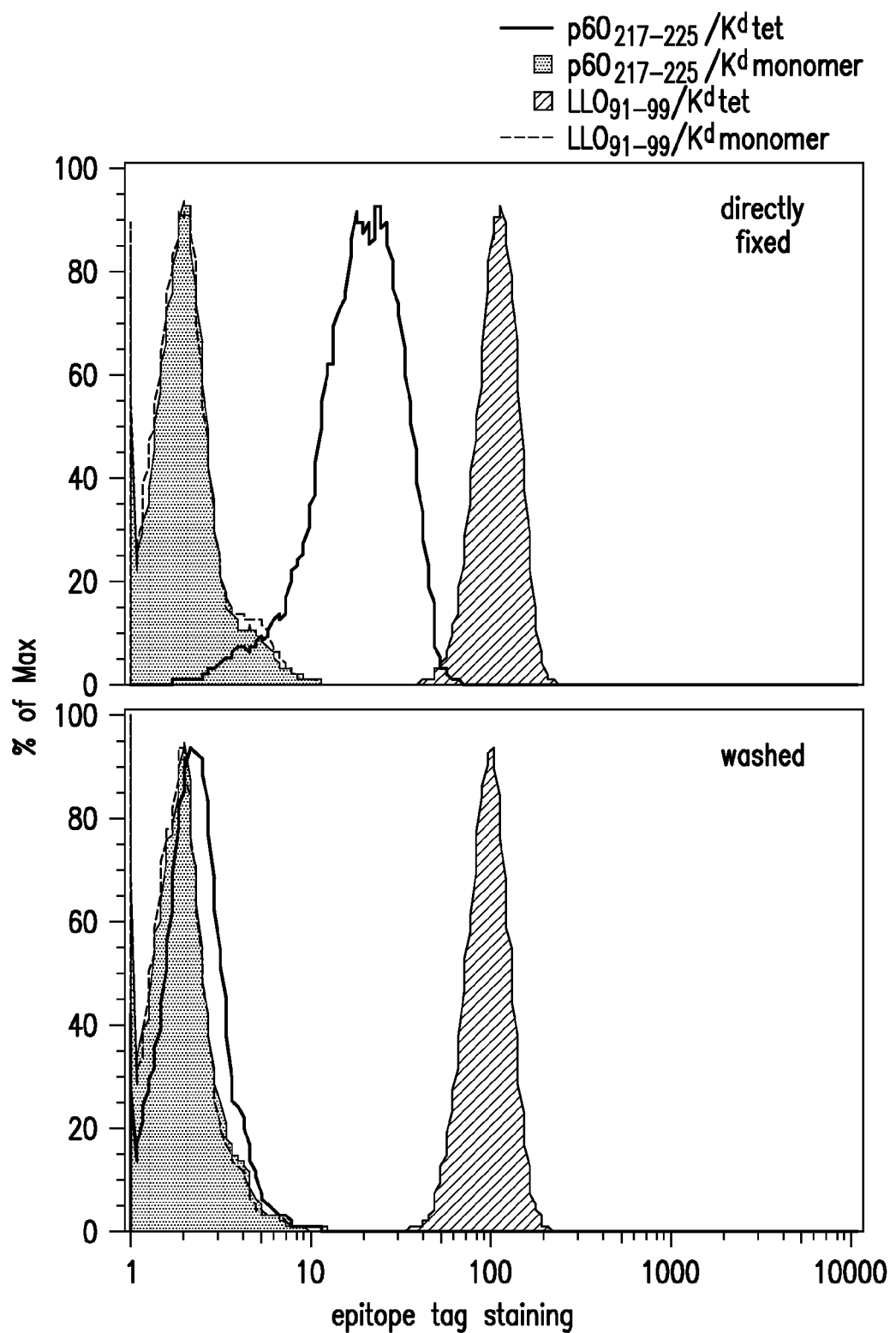
FIG. 5: Development of a reversible MHC multimer staining technology. (a) $LLO_{91-99}$-specific T cells were stained for 30 min with monomeric or tetrameric ("tet") $LLO_{91-99}$/H2-$K^d$/β$_2$m-HSV-tag or $p60_{217-225}$/H2-$K^d$/β$_2$m-HSV-tag reagents. Cells were fixed without washing (upper histogram) or after 2 washing steps (lower histogram) with 1% paraformaldehyde and subsequently stained for remaining HSV-epitope-tag on the cell surface (x-axis). (b+c) $LLO_{91-99}$-specific T cells were stained for 45 min with $LLO_{91-99}$/H2-$K^d$Strep-tag® II peptide/β$_2$-HSV-tag:Strep:Tactin® polypeptide polymers (IBA GmbH) ("poly"), briefly washed to remove unbound reagents, and incubated in the presence (b) or absence (c) of 1 mM d-biotin; all steps were performed at 4° C. Cell aliquots were harvested after different time intervals (indicated above histograms), fixed with 1% paraformaldehyde, and stained for remaining HSV-epitope-tag on the cell surface (x-axis).

MHC multimers increase the "relative binding avidity" but not the affinity of TCR-MHC/peptide interactions. Although epitope-specific T cells demonstrate some detectable interaction with monomeric MHC/epitope molecules when fixed immediately with paraformaldehyde (FIG. 5a, upper histogram), after brief washing all reagent-derived MHC monomers disappear from the cell surface (FIG. 5a, lower histogram, performed at 4° C.). Based on these observations, we postulated that targeted disruption of multimers into MHC monomers results in rapid dissociation of surface bound TCR ligand and—if all procedures performed at low temperatures—T cells might maintain the original functional status and phenotype (see model in FIG. 2).

Recently, a short peptide sequence (Strep-tag® II, IBA GmbH) has been identified that demonstrates binding affinity ($K_d$ approx. $10^{-6}$ M) for the biotin binding-site of a mutated streptavidin molecule, called "Strep:Tactin®" (IBA GmbH). The molecule d-biotin, which binds with higher affinity to Strep:Tactin® polypeptide (IBA GmbH) ($K_d$<$10^{-13}$M), effectively competes with Strep-tag® IIpeptide (IBA k GmbH) for the binding site. If MHC multimers based on the interaction of st-r-epStrep-tag® II peptide/Strep_Tactin® polypeptide (IBA GmbH) could be generated for T cell staining, it should thus be possible to competitively disrupt multimers in the presence of relatively low concentrations of d-biotin (see model in 5 FIG. 2).

Figure 5B:
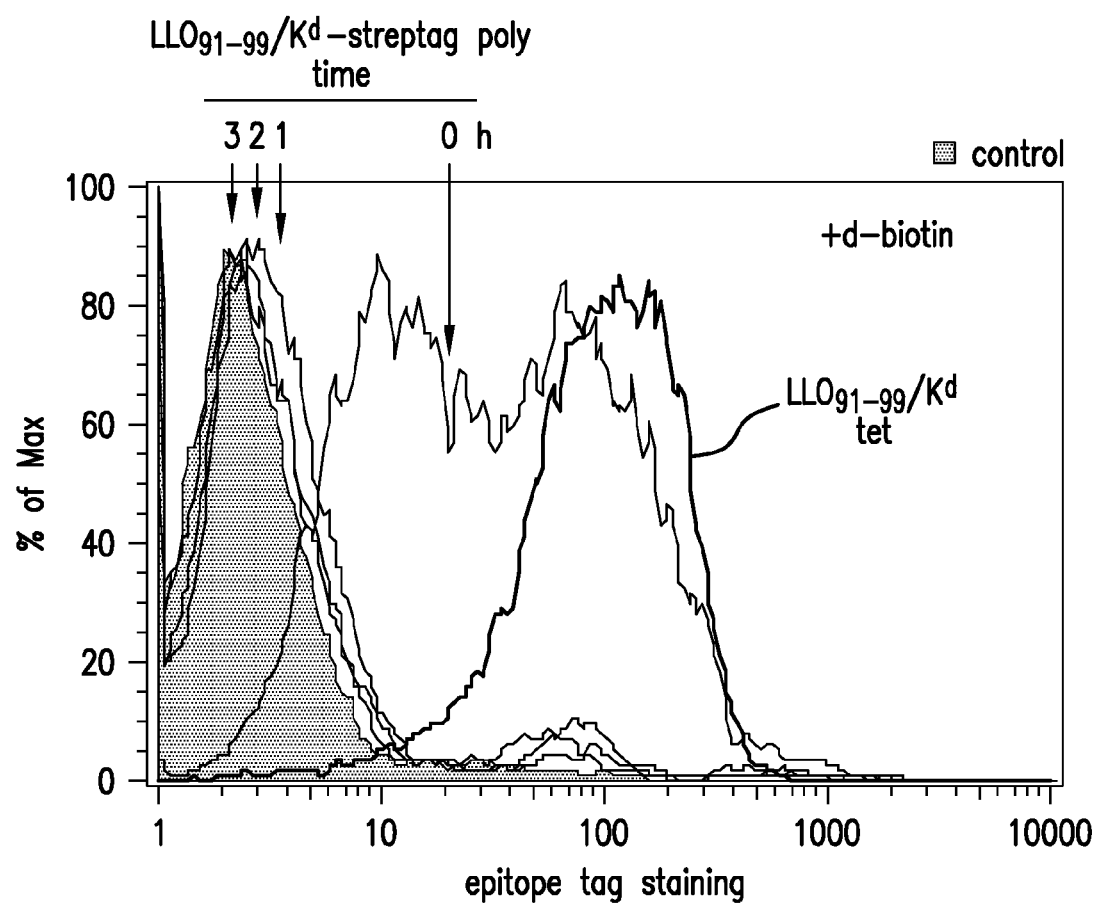
Figure 5C:
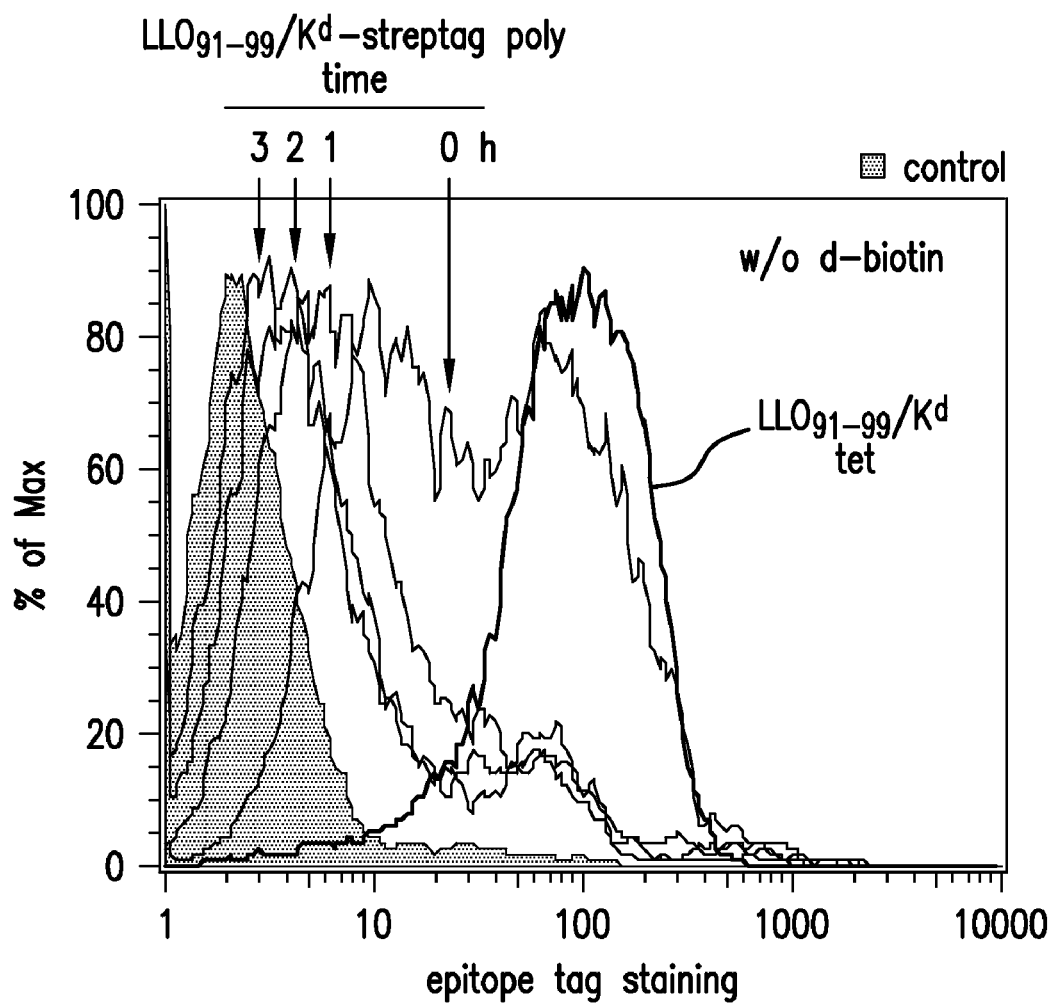
Figure 6:
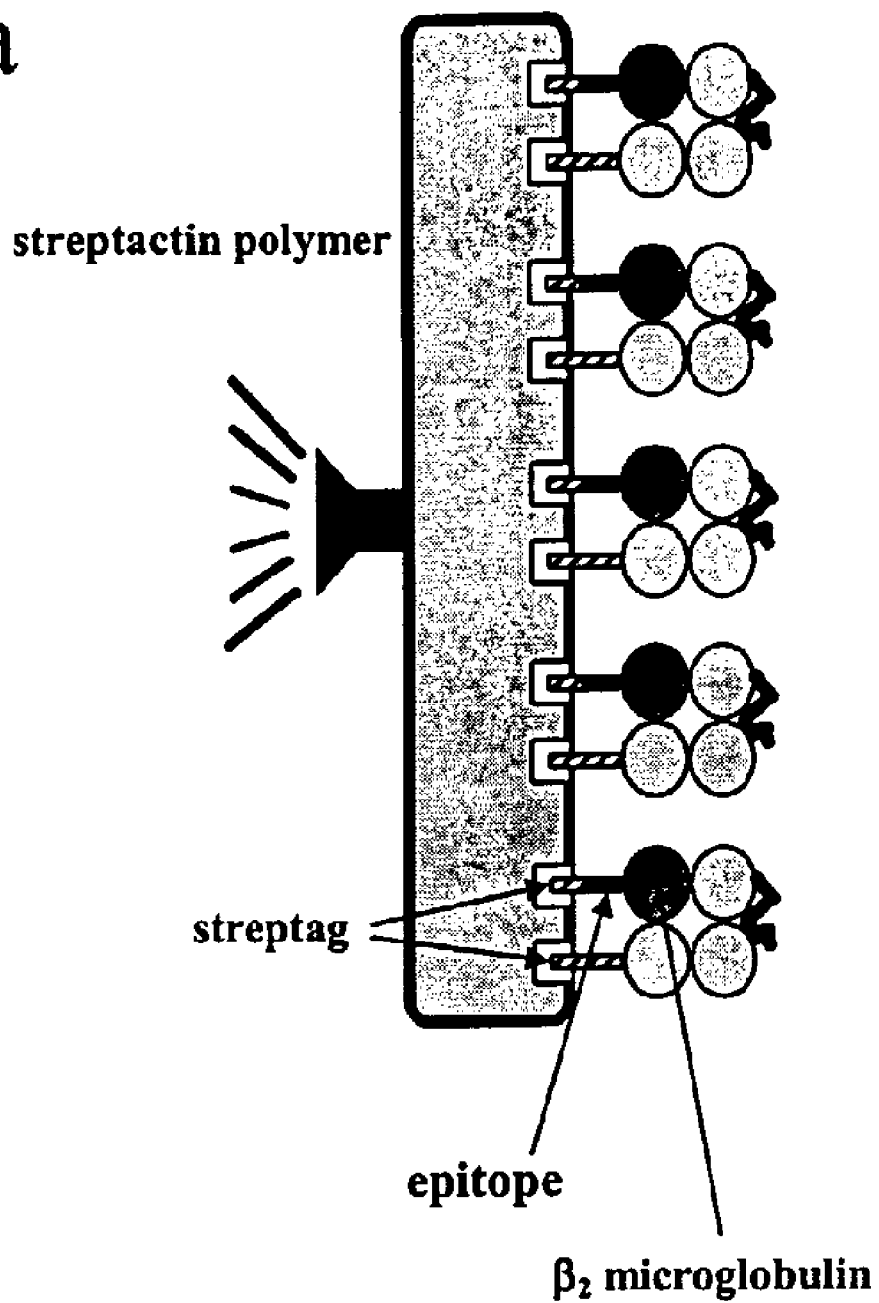
FIG. 6: Improvement of MHC-Strep-tag® II peptide/Strep-Tactin® polypeptide (IBA GmbH) multimer reagents. (a) Model for the stabilization of MHC-Strep-tag® II peptide (IBA GmbH) multimer reagents by fusion of so a second Strep-tag® II peptide (IBA GmbH) sequence to β$_2$-microglobulin. (b) $LLO_{91-99}$-specific T cells were stained for 45 min with $LLO_{91-99}$/H2 $K^d$Strep-tag® II peptide/β$_2$ Strep-tag® II peptide-HSV-tag-Strep:Tactin® polypeptide polymers (IBA GmbH) ("poly"), briefly washed to remove unbound reagents, and incubated in the presence (upper histogram) or absence (lower histogram) of 1 mM biotin. All steps were performed 4° C., cell aliquots were harvested after different time intervals (indicated above histograms), fixed with 1% paraformaldehyde, and stained for remaining HSV-epitope-tag on the cell surface (x-axis).
Figure 6B:
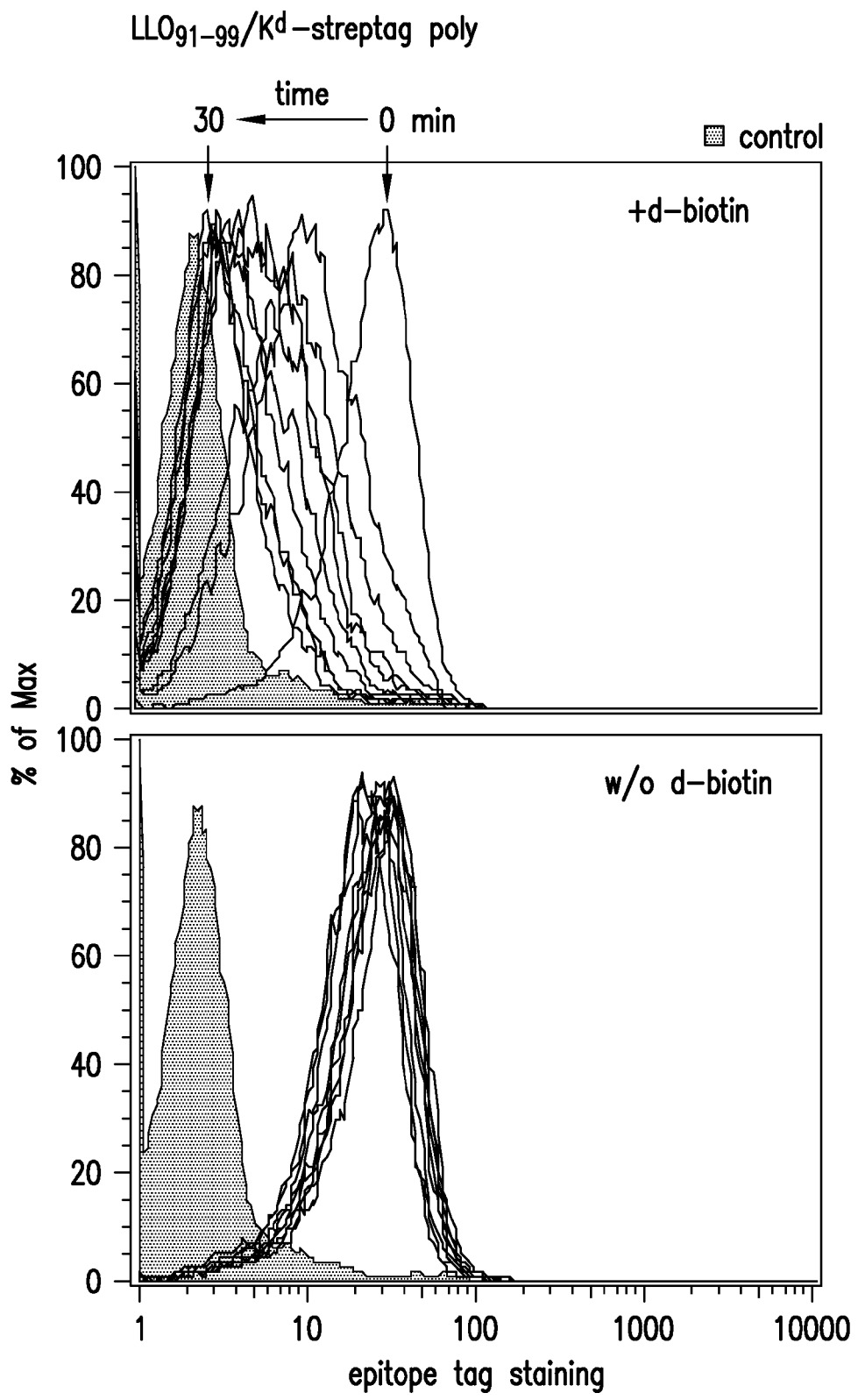

We generated soluble H2-$K^d$ Strep-tag® II peptide (IBA GmbH) fusion proteins; to be able to specifically detect recombinant MHC molecules, an epitope-tag sequence (HSV/gpD, Novagen) was fused to the C-terminus of $β_2$-microglobulin. These changes did not affect the binding specificity efor stability of in vitro folded MHC reagents (data not shown). MHC-trep-tag® II peptide (IBA GmbH) molecules incubated with Strep-Tactin® polypeptide (IBA GmbH)-polymers as 'backbone' for multimerization (kindly provided by IBA, Gottingen, Germany) demonstrated high intensity T cell staining (FIG. 5b), which rapidly decreased after incubation in the presence of d-biotin (1 mM, all at 4° C.). Unfortunately, staining with MHC Strep-tag® II peptide/Strep-Tactin® polypeptide (IBA GmbH) polymers also decreases over time in the absence of d-biotin, indicating instability of the reagents (FIG. 5c). To improve the stability of MHC Strep-tag® II peptide (IBA GmbH) multimers, an additional strep-tag® II peptide (IBA GmbH) was fused to the C-terminus of $β_2$-microglobulin (behind the HSV-tag, FIG. 6a). This strategy substantially improved the reagents; $LLO_{91-99}$/H2-$K^d$(2×) Strep-tag® II peptide Strep:Tactin® polypeptide (IBA GmbH)-polymer reagents stained $LLO_{91-99}$-specific T cells stably over time (FIG. 6b). Addition of d-biotin (1 mM, all at 4° C.) resulted in immediate and complete dissociation of the Strep:Tactin® polypeptide (IBA GmbH) polymer backbone (FIG. 6b and unpublished results). The amount of surface-bound, reagent-derived MHC molecules subsequently decreased rapidly (FIG. 6b).

Reversible MHC Multimer Staining

In order to test the effect of reversible MHC multimer staining on T cell function, in vitro expanded $LLO_{91-99}$-specific T cell lines were stained with $LLO_{91-99}$/H2-$K^d$(2×) Strep-tag® II peptide Strep-Tactin® polypeptide (IBA GmbH)-polymer reagents, and washed over 4 h in cold (4° C.) buffer containing d-biotin (1 mM) or no d-biotin. As controls, cells were pretreated with binding ($LLO_{91-99}$/H2-$K^d$) or non-binding ($p60_{217-227}$/H2-$K^d$) conventional tetramer reagents. No MHC Strep-tag® II peptide (IBA GmbH) multimer-derived MHC/$LLO_{91-99}$ molecules could be detected on the cell surface after incubation and washing in the presence of 1 mM d-biotin (FIG. 7a); under these conditions no phenotypic changes, like TCR downregulation or increased annexin V binding, could be observed; d-biotin was tested up to concentrations of 50 mM, and no evidence for toxicity or changes of T cell function were observed (data not shown). Testing of differently treated T cells in cytotoxicity assays (see also FIG. 3c) demonstrated high bystander lysis of MHC Strep-tag® II peptide (IBA GmbH) multimer-stained cells without dissociation (FIG. 7b, open squares); after dissociation of the reagents (open triangles), the cytotoxic T cell function is basically indistinguishable from controls (filled squares). The positive effect of reversible T cell staining is even more evident in proliferation assays. LLO$_{91-99}$-specific T cells responded poorly to antigen-specific or mitogenic stimulation when MHC multimer reagents remain on the cell surface (FIG. 7c); after dissociation of surface-bound MHC/LLO$_{91-99}$ complexes, proliferative responses of the cells were identical to control cells. Maintenance of in vivo function of MHC Strep-tag® II peptide (IBA GmbH) multimer-stained cells so was tested in adoptive transfer experiments. Pretreatment of LLO$_{91-99}$ specific T cells with conventional binding MHC tetramer reagents (FIG. 7d, open bar) resulted in significantly reduced protection towards Listeria infection following adoptive transfer. In contrast, after complete dissociation of reagent-derived MHC complexes, the same number of cells conferred almost an identical degree of protection as compared to positive controls. Interestingly, without dissociation of MHC Strep-tag® II peptide (IBA GmbH) multimers prior to adoptive cell transfer, the cells were reproducibly more effective than cells coated with conventional MHC tetramers. Since low levels of d-biotin are found in serum that can disrupt the backbone from MHC Strep-tag® II peptide (IBA GmbH) multimers (data not shown), it is likely that serum d-biotin may cause also some dissociation after in vivo transfer.

3. Discussion

Our data show that MHC multimers significantly change the phenotype and function of stained T cells at physiological temperatures. This is in accordance with recent findings by other groups demonstrating strong signaling events mediated through MHC multimer reagents, leading to overstimulation and cell death. To overcome this problem, we developed a reversible staining procedure that allows specific detection of antigen-specific T cells by surface staining at low temperatures. Addition of a competitor resulted in rapid disassembly of surface bound multimers and subsequent dissociation of monomeric MHC/peptide molecules from the T cell surface. Using this new technique, we find that the functional status of T cells can be maintained after their identification and purification.

Several factors are preferably considered in the development of a reversible T cell staining technique: (1) Rapid and complete monomerization should be accomplished at low temperatures [preferably at 4° C.]; (2) the procedure should be non-toxic to T cells; and (3) the substances used should be harmless for (clinical) in vivo applications.

The MHC Strep-tag® II peptide (IBA GmbH) multimer system fulfills all these requirements: (1) Because of the extreme affinity differences between Strep-tag® II peptide/Strep-Tactin® polypeptide (IBA GmbH) and d-biotin/Strep-Tactin® polypeptide (IBA GmbH), complete and very fast competitive binding is achieved even at low temperatures; (2) d-biotin (vitamin H) in low concentrations is non-toxic for T cells; we tested d-biotin up to a concentration of 50 mM and could not find evidence for toxicity or changes of T cell function; (3) the amounts of d-biotin that might be transferred together with reversibly stained T cells are far lower than d-biotin concentrations found in conventional vitamin supplementations and are therefore unlikely to be harmful.

Figure 7:
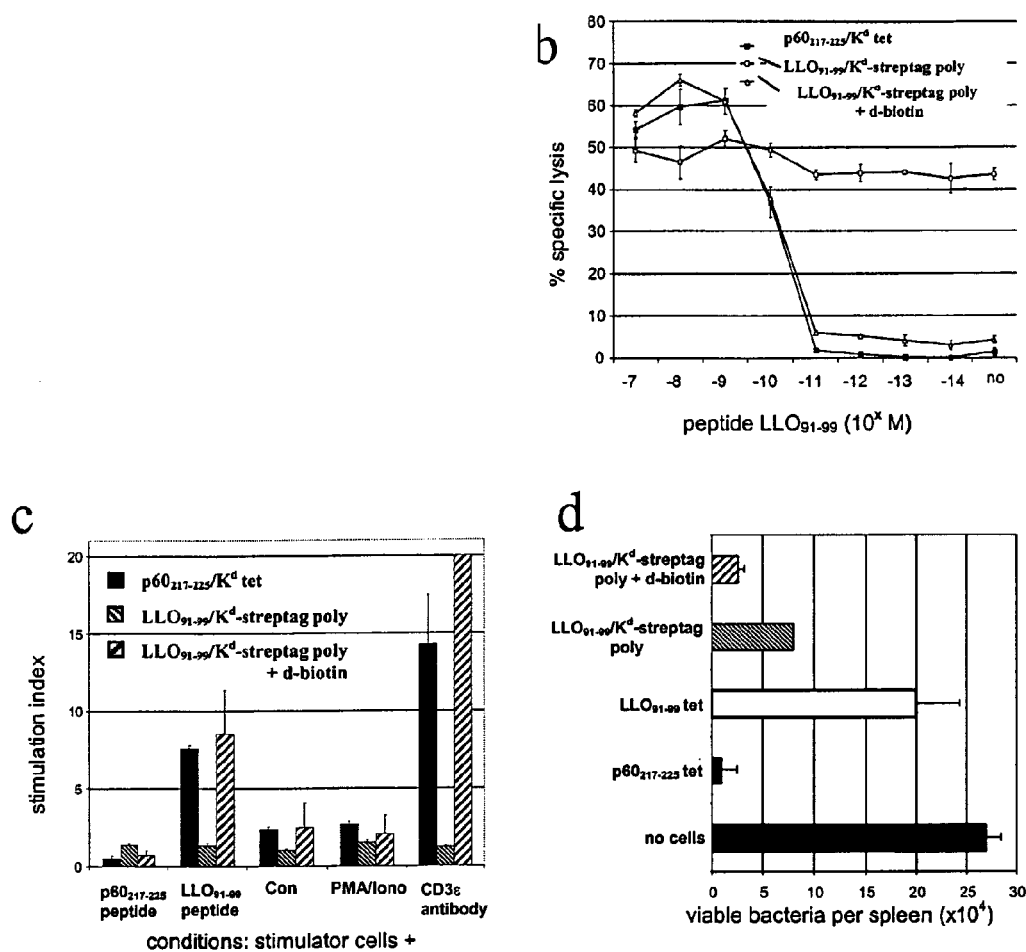

Our data show that the reversible staining procedure maintains the phenotypical and functional status of T cell populations. T cell function is not significantly affected (see FIG. 7). After dissociation of surface bound MHC/peptide complexes, there is no reagent left on the cells. With prior art antibody-based staining and isolation procedures the marker remains on positively stained populations, potentially influencing T cell function and affecting the success of in vivo applications; adverse (e.g. allergic) reactions might be induced through Fc-receptor-mediated mechanisms or the fluorescence marker itself. Reversible MHC multimer staining avoids these potential complications, which we view as further advantage of this technology for in vivo applications.

We were particularly impressed by the deleterious effects of conventional MHC tetramer staining on the outcome of adoptive transfer experiments, a problem overcome by the reversible T cell staining procedure described here. Direct ex vivo isolation (e.g. by fluorescence-activated (FACS) or magnetically-activated cell separation) and adoptive transfer of defined antigen-specific T cell populations could now be realized as a very effective therapeutic strategy. For example adoptive transfer of EBV- and/or CMV-specific T cell populations during (otherwise) T cell-depleted stem cell transplantations is likely to reduce the incidence of EBV and CMV-related malignancies in transplant patients. Purification of antigen-specific T cells also plays an important role in the improvement of T cell cloning strategies, especially when purified antigen-specific cells need to be further expanded by effective antigen-independent stimuli (mitogens or anti-CD3). We are in the process of generating human HLA Strep-tag® II peptide (IBA GmbH) fusion proteins and directly fluorochrome- or magnetic-bead-conjugated Strep-Tactin® polypeptide (IBA GmbH) to test potential clinical applications. Furthermore, the basis principle of the reversible multimer-staining procedure might be applicable to other low avidity receptor-ligand interactions.

REFERENCES

1. Miyahira, Y., K. Murata, D. Rodriguez, J. R. Rodriguez, M. Esteban, M. M. Rodriguez, and F. Zavala. 1995. Quantification of antigen specific CD8+ T cells using an ELISPOT assay. *J. Immunol. Methods* 181:45-54.
2. Murali-Krishna, K., J. D. Altman, M. Suresh, D. J. D. Sourdive, A. J. Zajac, J. D. Miller, J. Slansky, and R. Ahmet. 1998. Counting antigen-specific CD8 T cells: a reevaluation of bystander activation during viral infection. *Immunity* 8:177-187.
3. Manz, R., M. Assenmacher, E. Pfluger, S. Miltenyi, and A. Radbruch. 1995. Analysis and sorting of live cells to secreted molecules, relocated to a cell-surface affinity matrix. *PNAS* 92:1921-1925.
4. Altman, J. D., P. A. H. Moss, P. J. R. Goulder, D. H. Barouch, M. G. McHeyzer-Williams, J. I. Bell, A. J. McMichael, and M. M. Davis. 1996. Phenotypic analysis of antigen specific T lymphocytes. *Science* 274:94-96.
5. Busch, D. H., I. M. Pilip, S. Vijh, and E. G. Pamer. 1998. Coordinate regulation of complex T cell populations responding to bacterial infection. *Immunity* 8:353-362.
6. Pamer, E., and P. Cresswell. 1998. Mechanisms of MHC class I-restricted antigen processing. *Annu. Rev. Immunol.* 16:323-358.
7. McMichael, A., and C. O'Callaghan. 1998. A new look at T cells. *J Exp Med* 187:1367-1371.
8. Doherty, P. 1998. The numbers game for virus-specific CD8+ T cells. *Science* 280:227.
9. Schmidt, T., and A. Skerra. 1993. The random peptide library-assisted engineering of a C-terminal affinity peptide, useful for the detection and purification of a functional Ig Fv fragment. *Protein Eng* 6:109-122.

10. Schmidt, T., J. Koepke, R. Frank, and A. Skerra. 1996. Molecular interaction between the strep-tag affinity peptide and its cognate target, streptavidin. *J Mol Biol* 9:753-766.
11. Voss, S., and A. Skerra. 1997. Mutagenesis of a flexible loop in streptavidin leads to higher affinity for the Strep-tag II peptide and improved performance in recombinant protein purification. *Protein Eng* 10:975-982.
12. Savage, P. A., J. J. Boniface, and M. M. Davis. 1999. A kinetic basis for the T cell receptor repertoire selection during an immune response. *Immunity* 10:485-492.
13. Busch, D. H., and E. G. Pamer. 1998. T cell affinity maturation by selective expansion during infection. *J Exp Med* 189:701-709.
14. Van der Merwe, P. A., M. H. Brown, S. J. Davis, and A. N. Barclay. 1993. Affinity and kinetic analysis of the interaction of the cell adhesion molecules rat CD2 and CD48. *EMBO J.* 12:4945-54.
15. Al-Shamkhani A., S. Mallett, M. H. Brown, W. James, and A. N. Barclay. 1997. Affinity and kinetics of the interaction between soluble trimeric OX40 ligand, a member of the tumor necrosis family, and its receptor OX40 on activated T cells. *J Biol Chem* 272:5275-82.
16. Garboczi D. N., D. T. Hung and D. C. Wiley. 1992. HLA-A2-peptide complexes: refolding and crystallization of molecules expressed in *Escherichia coli* and complexed with single antigenic peptides. *Proc Natl Acad Sci USA* 89:3429-3433.
17. Scott C. A., K. C. Garcia, F. R. Carbone, I. A. Wilson, L. Teyton. 1996. Role of chair pairing for the production of functional soluble IA major histocompatibility complex class II molecules. *J Exp Med* 183:2087-2095.
18. Busch D. H., and E. G. Pamer. 1998. MHC class I/peptide stability: implications for immunodominance, in-vitro proliferation, and diversity of responding CTL. *J Immunol* 160: 4441-4448.

What is claimed is:

1. A method for the reversible staining of a target cell, said target cell comprising a receptor molecule on its surface, with a detectable label, the method comprising:

A) contacting a sample of cells comprising said target cell with
   (i) a receptor molecule binding reagent comprising (a) a ligand which specifically binds to said receptor molecule to form a first binding pair and (b) a first partner of a second binding pair, wherein said ligand and said receptor molecule exhibit a binding interaction having a dissociation constant ($K_d$) in the range of $10^{-2}$ to $10^{-7}$ M, and wherein said first partner binds to a second partner to form a first partner: second partner second binding pair,
   (ii) a second partner which forms part of said first partner: second partner second binding pair, wherein said second partner has at least two binding sites for said first partner, each binding site capable of forming a reversible bond with said first partner, wherein the dissociation constant ($K_d$) of said reversible bond is in the range of $10^{-2}$ to $10^{-13}$ M, and
   wherein multivalent complexes that bind to said target cell are formed by the binding of at least two said ligand-containing receptor molecule binding reagents to one said second partner, said multivalent complexes providing increased avidity, relative to the binding of a single ligand to said target cell, due to the presence on each multivalent complex of at least two of said ligand-containing receptor molecule binding reagents; and
   (iii) said detectable label, wherein said detectable label is bound to or binds to said ligand-containing receptor molecule binding reagent and/or said second partner, wherein said target cell is stained by binding of said multivalent complexes to said target cell, and wherein staining of said target cell is reversible upon disruption of the reversible bond between said first partner and said second partner.

2. The method of claim 1 further comprising separating said stained cell from non-target cells present in said sample.

3. The method of claim 1 further comprising removing said staining from said cell by disrupting the binding between said first partner and said second partner.

4. The method of claim 1, wherein
   (a) said first partner comprises biotin and said second partner is a streptavidin analog or an avidin analog that reversibly binds to biotin,
   (b) said first partner comprises a biotin analog that reversibly binds to streptavidin or avidin and said second partner is streptavidin, avidin, a streptavidin analog, or an avidin analog that reversibly binds to said biotin analog, or
   (c) said first partner comprises a streptavidin or avidin binding peptide and said second partner is streptavidin, avidin, a streptavidin analog, or an avidin analog that reversibly binds to said streptavidin or avidin binding peptide.

5. The method of claim 4, wherein said first partner comprises the streptavidin-binding peptide Trp-Ser-His-Pro-Gln-Phe-Glu-Lys (SEQ ID NO: 2) and said second partner comprises the streptavidin analog Val$^{44}$-Thr$^{45}$-Ala$^{46}$-Arg$^{47}$ (SEQ ID NO: 4) or the streptavidin analog Ile$^{44}$-Gly$^{45}$-Ala$^{46}$-Arg$^{47}$ (SEQ ID NO: 3).

6. The method of claim 1, wherein the binding between said first partner and said second partner occurs in the presence of a divalent cation.

7. The method of claim 6, wherein said first partner is a calmodulin binding peptide and said second partner is a polymer of calmodulin.

8. The method of claim 6, wherein said first partner is a FLAG peptide and said second partner is an antibody binding the FLAG peptide.

9. The method of claim 6, wherein the binding between said first partner and said second partner is disrupted by metal ion chelation.

10. The method of claim 9, wherein the metal ion chelation is accomplished by addition of EDTA.

11. The method of claim 1, wherein said second partner is an oligomer or a polymer of streptavidin or avidin or of any analog of streptavidin or avidin.

12. The method of claim 11, wherein the oligomer or polymer is crosslinked by a polysaccharide.

13. The method of claim 1, wherein said first partner is an antigen and said second partner an antibody against said antigen.

14. The method of claim 3, wherein removal of the staining results in a dissociation of the receptor molecule binding reagent from the stained cell.

15. The method of claim 1, wherein said ligand which specifically binds to said receptor molecule is selected from the group consisting of an antibody, an antibody fragment, an engineered lipocalin, and a major histocompatibility On MHC molecule.

16. The method of claim 1, wherein said contacting is carried out at a temperature of <15° C.

17. The method of claim 1, wherein said target cell is a mammalian cell.

18. The method of claim 1, wherein the detectable label is a fluorescent dye or a magnetic label.

19. The method of claim 1, wherein the ligand comprises a single binding site for said receptor molecule.

* * * * *

UNITED STATES PATENT AND TRADEMARK OFFICE
CERTIFICATE OF CORRECTION

PATENT NO. : 8,298,782 B2  
APPLICATION NO. : 12/843763  
DATED : October 30, 2012  
INVENTOR(S) : Dirk H. Busch et al.

Page 1 of 1

It is certified that error appears in the above-identified patent and that said Letters Patent is hereby corrected as shown below:

Column 24, lines 7 - 8, claim 15, delete the text "On MHC" and replace with --(an MHC)--.

Signed and Sealed this  
Nineteenth Day of February, 2013

Teresa Stanek Rea  
*Acting Director of the United States Patent and Trademark Office*